(12) United States Patent
Stout et al.

(10) Patent No.: US 9,222,068 B2
(45) Date of Patent: Dec. 29, 2015

(54) APPARATUS FOR AND METHOD OF PREPARING PLANT TISSUE FOR PLANT PRODUCTION

(71) Applicant: ArborGen Inc., Ridgeville, SC (US)

(72) Inventors: Timothy Stout, Summerville, SC (US); John Clark, Summerville, SC (US); Sydney Seymour, Cary, NC (US); Ronald Winkles, Summerville, SC (US)

(73) Assignee: Arborgen, Inc., Summerville, SC (US)

( * ) Notice: Subject to any disclaimer, the term of this patent is extended or adjusted under 35 U.S.C. 154(b) by 117 days.

(21) Appl. No.: 14/076,965

(22) Filed: Nov. 11, 2013

(65) Prior Publication Data

US 2014/0134664 A1  May 15, 2014

Related U.S. Application Data

(62) Division of application No. 12/679,616, filed as application No. PCT/US2008/010988 on Sep. 23, 2008, now Pat. No. 8,580,566.

(60) Provisional application No. 60/960,282, filed on Sep. 24, 2007.

(51) Int. Cl.
| | |
|---|---|
| *C12N 5/00* | (2006.01) |
| *C12N 5/04* | (2006.01) |
| *A01H 4/00* | (2006.01) |
| *C12M 3/00* | (2006.01) |
| *C12M 1/00* | (2006.01) |

(52) U.S. Cl.
CPC *C12N 5/04* (2013.01); *A01H 4/001* (2013.01); *C12M 21/06* (2013.01); *C12M 23/48* (2013.01); *C12M 23/50* (2013.01)

(58) Field of Classification Search
USPC .......................................................... 435/420
See application file for complete search history.

(56) References Cited

U.S. PATENT DOCUMENTS

| | | | |
|---|---|---|---|
| 3,060,660 A | 10/1962 | Reading | |
| 3,386,224 A | 6/1968 | Shuttleworth | |
| 3,406,837 A | 10/1968 | Kirsch et al. | |
| 4,557,659 A | 12/1985 | Scaglia | |
| 4,627,785 A | 12/1986 | Monforte | |
| 4,720,227 A | 1/1988 | Eberle | |
| 4,801,429 A | 1/1989 | Torfs et al. | |
| 5,088,231 A * | 2/1992 | Kertz | 47/1.01 R |
| 5,344,202 A | 9/1994 | Ramler | |
| 6,730,471 B1 * | 5/2004 | Katerkamp et al. | 435/4 |
| 6,852,525 B1 | 2/2005 | Cantor | |
| 7,015,032 B2 * | 3/2006 | Adelberg et al. | 435/308.1 |
| 7,090,559 B2 | 8/2006 | Vulich et al. | |
| 7,210,246 B2 | 5/2007 | Van Der Meulen | |
| 7,665,243 B2 | 2/2010 | Nehra et al. | |

FOREIGN PATENT DOCUMENTS

| | | |
|---|---|---|
| EP | 0 132 414 A2 | 1/1985 |
| WO | WO-90/06058 A1 | 6/1990 |
| WO | WO 92/03913 A1 | 3/1992 |
| WO | WO 95/20645 A1 | 9/1995 |
| WO | WO-2006/118962 A2 | 11/2006 |

OTHER PUBLICATIONS

International Search Report of the corresponding International Patent Application PCT/US08/10988.
Supplemental European Search Report received in the related European Patent Application No. EP 08834477, dated Jan. 3, 2012.

* cited by examiner

*Primary Examiner* — Annette Para
(74) *Attorney, Agent, or Firm* — Foley & Lardner LLP

(57) ABSTRACT

An apparatus for preparing multiple plant embryos for plant production includes a first station having a first rack system configured to support at least one incubation vessel, a second station having an automated member configured to manipulate the at least one incubation vessel and a third station having a second rack system configured to support the at least one incubation vessel after being manipulated by the automated member. The second station can be selectively adjusted to perform more than one operation required in the development of plant embryos.

12 Claims, 10 Drawing Sheets

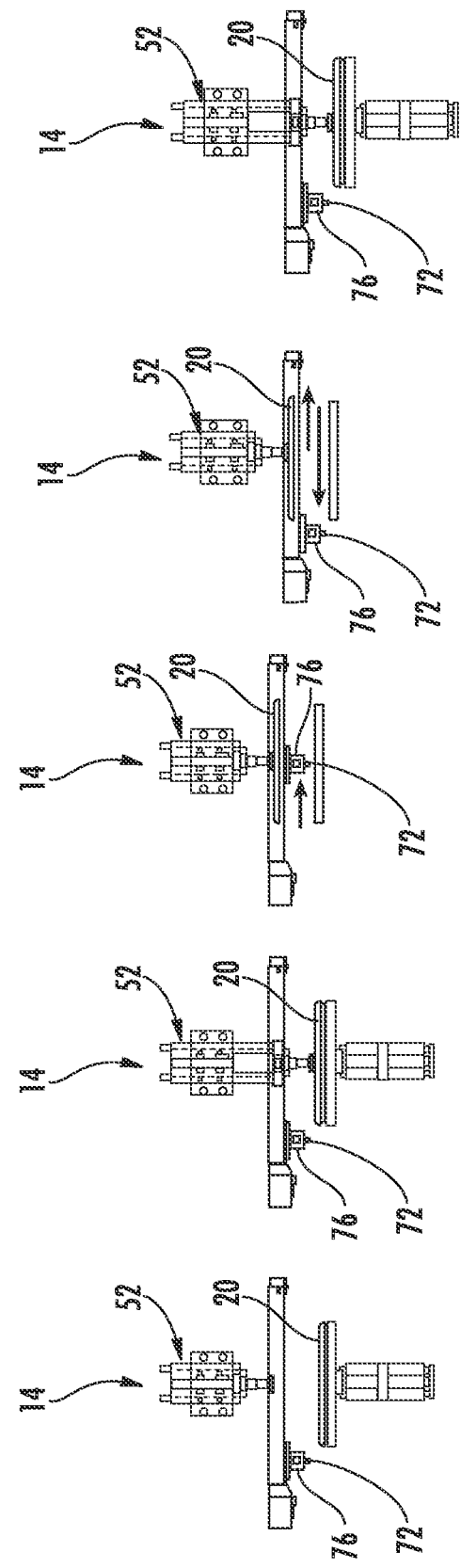

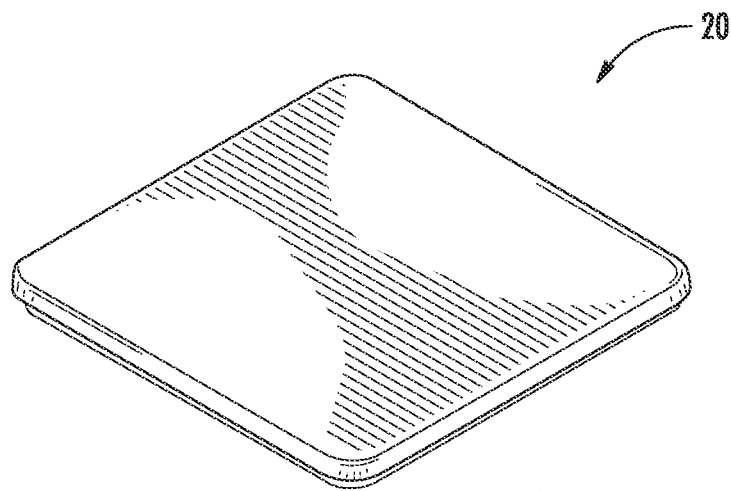
FIG. 13
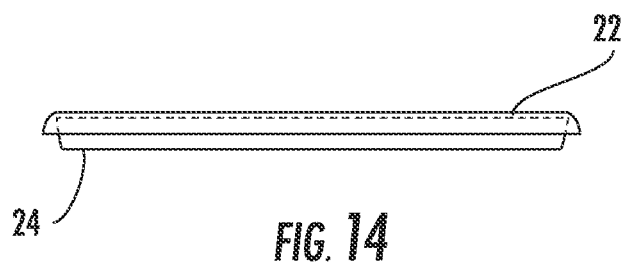
FIG. 14
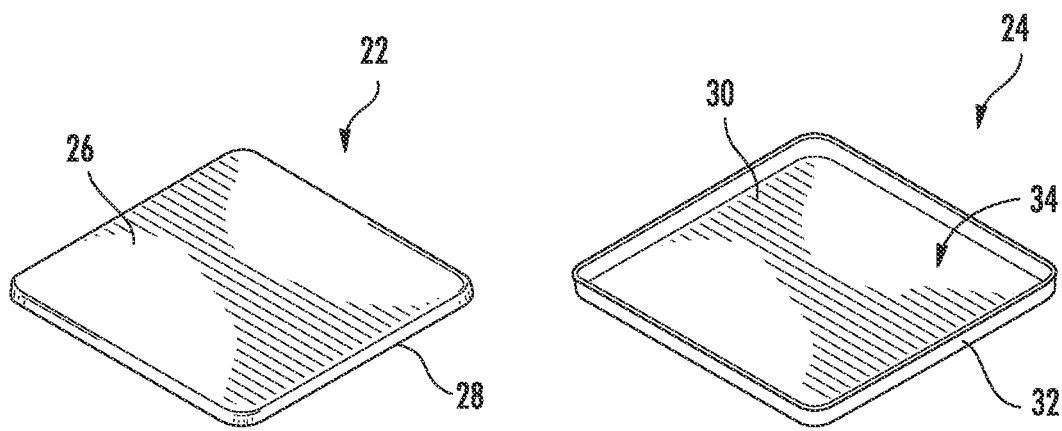
FIG. 15
FIG. 16

APPARATUS FOR AND METHOD OF PREPARING PLANT TISSUE FOR PLANT PRODUCTION

CROSS REFERENCE TO RELATED PATENT APPLICATIONS

The present application is a division of U.S. application Ser. No. 12/679,616, filed Jun. 29, 2010, now U.S. Pat. No. 8,580,566, which is the National Phase of International Patent Application No. PCT/US2008/010988, filed Sep. 23, 2008, which claims the benefit of U.S. Provisional Application No. 60/960,282, having a filing date of Sep. 24, 2007, titled "APPARATUS FOR AND METHOD OF PREPARING PLANT TISSUE FOR PLANT PRODUCTION. The contents of these applications are herein incorporated by reference in their entirety.

BACKGROUND

The present disclosure relates generally to an apparatus for and a method of preparing plant tissue (e.g., somatic embryos, embryogenic tissue, organogenic tissue, vegetative tissue, seeds, etc.) for plant production. More particularly, the present disclosure relates to an at least partially automated apparatus for and a method of preparing plant tissue for plant production.

The process of preparing plant tissue, such as somatic embryos, for plant production (e.g., in the case of conifer treatment, etc.) generally includes the following steps: 1) cone collection and storage; 2) somatic embryogenic initiation on an initiation medium; 3) maintenance of embryogenic tissue on a maintenance medium; 4) cryogenic storage of embryogenic tissue and subsequent cryoretrieval; 5) growth of embryogenic tissue; 6) development of somatic embryos on an embryo development medium; 7) harvesting of embryos; 8) conditioning of harvested embryos; and 9) germination.

Plating, inspecting, treating, collecting and/or storing of plant embryos prior to germination are key operations in many steps of the plant production process. The activities necessary for performing these operations, however, are usually performed by hand. For example, individual embryos are typically transferred to and from various media and vessels and must be plated onto media, one by one using forceps and often with the guidance of a dissecting microscope.

Such methods are burdensome, time-consuming, costly, and susceptible to contamination. Not only that, but only a limited number of embryos can be plated, inspected, treated and/or collected by a single person during a given period of time. Accordingly, any attempt to increase the number of embryos that can be produced and subsequently conditioned for germination necessarily requires an increase in manpower, which itself can be costly and often impractical.

There have been attempts to automate certain steps in the production of plant embryos. For example, U.S. Publication No. 2006/0260015, titled "Somatic Embryogenesis and Embryo Harvesting and Method and Apparatus for Preparing Plant Embryos for Plant Production" and assigned to Arbor-Gen, LLC, the entire disclosure of which is hereby incorporated by reference, discloses an at least partially automated apparatus for washing and harvesting plant embryos. There have also been attempts to automate the inspection of plant embryos. However, prior attempts to automate steps within the production process require a separate piece of equipment to perform the particular step to be automated. Since the production of plant embryos involves multiple steps, requiring a separate piece of equipment for each step would be costly.

Accordingly, there is a need in the agricultural industry and, in particular, the forestry sciences, for an apparatus for and a method of reducing human intervention within the plant production process. Reducing human intervention may reduce the likelihood of contamination and/or may provide for a more efficient system (e.g., one that can be readily scaled-up for commercial purposes, etc.). There is also a need for an apparatus that is capable of performing more than one step within the production process so that the amount of equipment needed to provide for an at least partially automated process (and the cost associated therewith) can be reduced.

SUMMARY

One exemplary embodiment relates to an apparatus for preparing plant tissue for plant production. The apparatus comprises a first station including a first rack system configured to support at least one culture vessel, a second station including an automated member configured to manipulate the at least one culture vessel and a third station having a second rack system configured to support the at least one culture vessel after being manipulated by the automated member.

Another exemplary embodiment relates to an apparatus for preparing plant tissue contained within a culture vessel for plant production. The apparatus comprises a member configured to move the culture vessel between an open position and a closed position, a delivery system configured to dispense a substance to the culture vessel when in the open position, an imaging system configured to capture an image of the plant tissue and a controller coupled to the member, the delivery system and the imaging system for automating the operation of each.

Another exemplary embodiment relates to a method of preparing plant tissue for plant production. The method comprises the steps of transporting a first culture vessel from a first station to a second station, manipulating the first culture vessel between a closed position and an open position, supplying at least one substance to the first culture vessel and controlling with a controller the steps of transporting, manipulating and supplying.

Another exemplary embodiment relates to a method of preparing plant tissue for plant production. The method comprises the steps of transporting a first culture vessel from a first station to a second station, performing a first operational step on the first culture vessel at the second station, controlling with a controller the steps of transporting the first culture vessel and performing the first operational step and reconfiguring at least one of the second station and the controller so that a second operational step can be performed on the first culture vessel at the second station. The second operational step is different than the first operational step.

BRIEF DESCRIPTION OF THE DRAWINGS

FIGS. 12A through 12E are schematics illustrating a dispensing sequence of operation according to an exemplary embodiment.

FIG. 13 is a perspective view of a culture vessel for use with the plant tissue production apparatus of FIG. 1 shown according to an exemplary embodiment.

FIG. 14 is a side elevation view of the culture vessel of FIG. 13.

FIG. 15 is a perspective view of a top portion of the culture vessel of FIG. 13.

FIG. 16 is a perspective view of a bottom portion of the culture vessel of FIG. 13.

DETAILED DESCRIPTION

Figure 1:
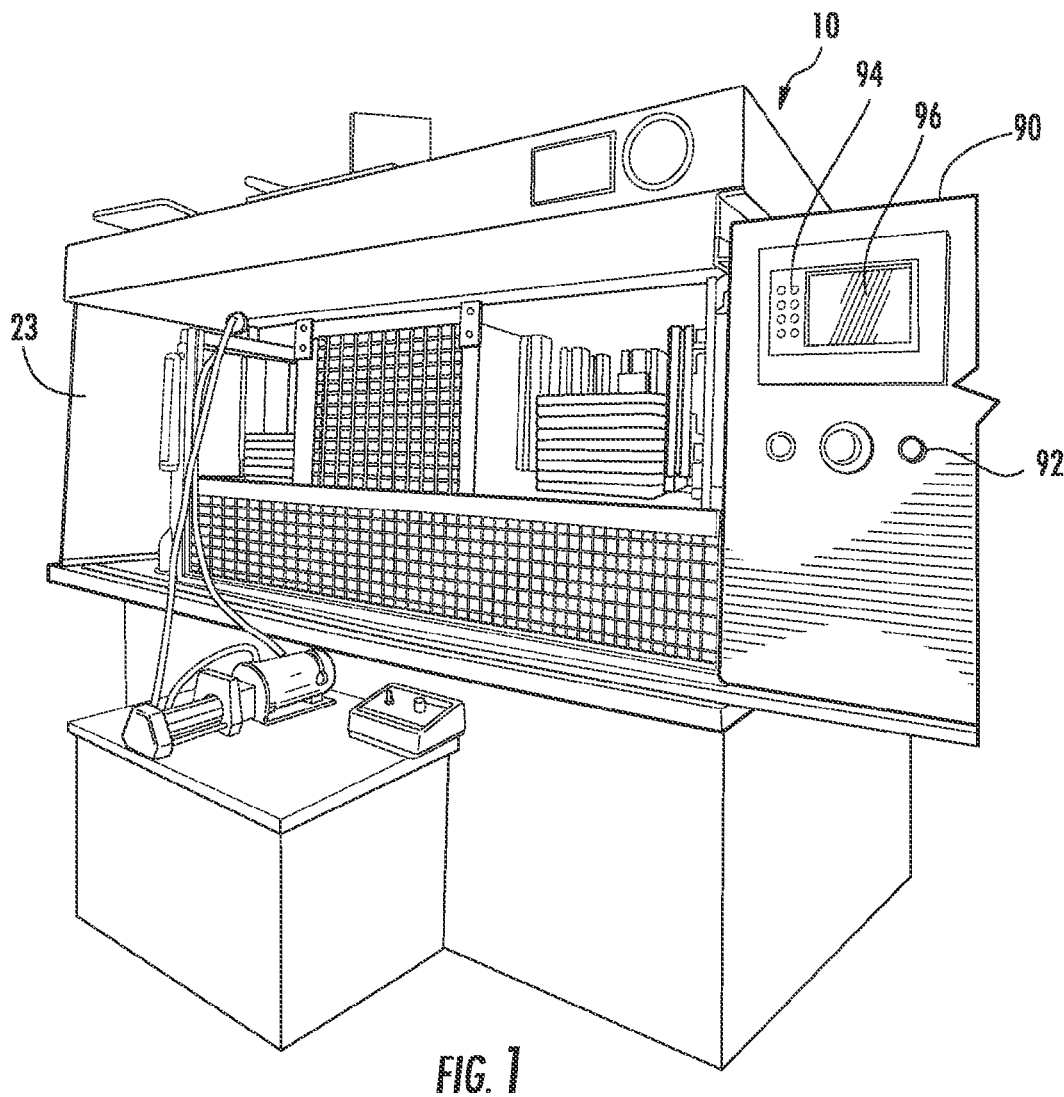
FIG. 1 is a perspective view of a plant tissue production apparatus shown according to an exemplary embodiment.

Referring generally to the FIGURES, an apparatus is provided that is useful in preparing plant tissue (e.g., somatic embryos, embryogenic tissue, organogenic tissue, vegetative tissue, seeds, etc.) for production (e.g., large-scale or commercial production, etc.). The apparatus, referred to broadly herein as a plant tissue production apparatus, is a multifunctional and at least partially controlled or automated (e.g., semi-automated, fully-automated, etc.) machine capable of performing operations required in the development and/or production of plant tissue. The plant tissue production apparatus is configured to be adjustable (e.g., configurable, reconfigurable, programmable, reprogrammable, etc.) so that it can perform more than one of the operations required at the various steps in the plant tissue production process.

For example, the plant tissue production apparatus may be selectively adjusted to perform one or more of the following operations: 1) media plating; 2) tissue plating; 3) process and/or plant tissue inspection; 4) quality assessment; and 5) sorting. For purposes of the present disclosure, media plating refers to the transferring of a base media (e.g., an initiation media, a maintenance media, a development media, etc.) to a vessel; tissue plating refers to the transferring of a plant tissue (e.g., a suspension culture, a gelled culture, etc.) to the base media; process and/or plant tissue inspection refers to obtaining an image or other characteristic of the process and/or plant tissue during development; quality assessment refers to using the image or other characteristic of the plant tissue to determine its quality based upon predetermined parameters; and sorting refers to the collection plant tissue either individually or en masse.

According to an exemplary embodiment, the plant tissue production apparatus is capable of performing all of the above-mentioned operations due to its adjustability (e.g., modularity, flexibility, etc.). Since the time between steps (e.g., lag time, development period, conditioning period, etc.) is typically a sizable time period, providing a machine that performs multiple steps reduces the likelihood that the machine will stay idle or unused between the steps. The plant tissue production apparatus may also be configured to provide developed or partially developed plant tissue to another apparatus or module, such as an embryo harvesting system of the type disclosed in U.S. Publication No. 2006/0260015 (referenced above) or any other apparatus for which it may be desirable to combine with the plant tissue production apparatus.

Providing an at least partially automated apparatus capable of performing more than one operation by being adjustable may advantageously reduce the number of machines required to automate the production of plant tissue thereby reducing equipment costs. Also, providing an at least partially automated apparatus capable of performing an operation required for the production of plant tissue may advantageously improve the efficiency and plant tissue production rates relative to hand-operated systems. For example, providing an at least partially automated apparatus capable of performing an operation required for the production of plant tissue that would otherwise need to be done manually may improve the quality of the plant tissue, reduce the amount of time needed to produce the plant tissue, reducing the amount of contaminated plant tissues, or increase the overall yield of plant tissue. Such efficiency may be realized in any phase or operation performed in the development process (e.g., plating, inspecting, harvesting, etc.).

Referring to FIGS. 1-4 in particular, a plant tissue production apparatus 10 is shown according to an exemplary embodiment. Apparatus 10 generally includes a first or input station 12, a second or operational station 14 and a third or output station 16. Apparatus 10 also includes a transport system 18 configured to selectively transport (e.g., deliver, move, etc.) one or more receptacles (e.g., containers, trays, plates, Petrie dishes, etc.), shown as incubation or culture vessels 20, between input station 12, operational station 14 and output station 16. It should be noted that the outset that apparatus 10 may include any number of operational stations or modules between the input and output stations. The addition of more than one operational station or module within the system may allow for more flexibility and/or greater throughput by providing multiple (e.g., different, etc.) operations simultaneously.

Figure 5:
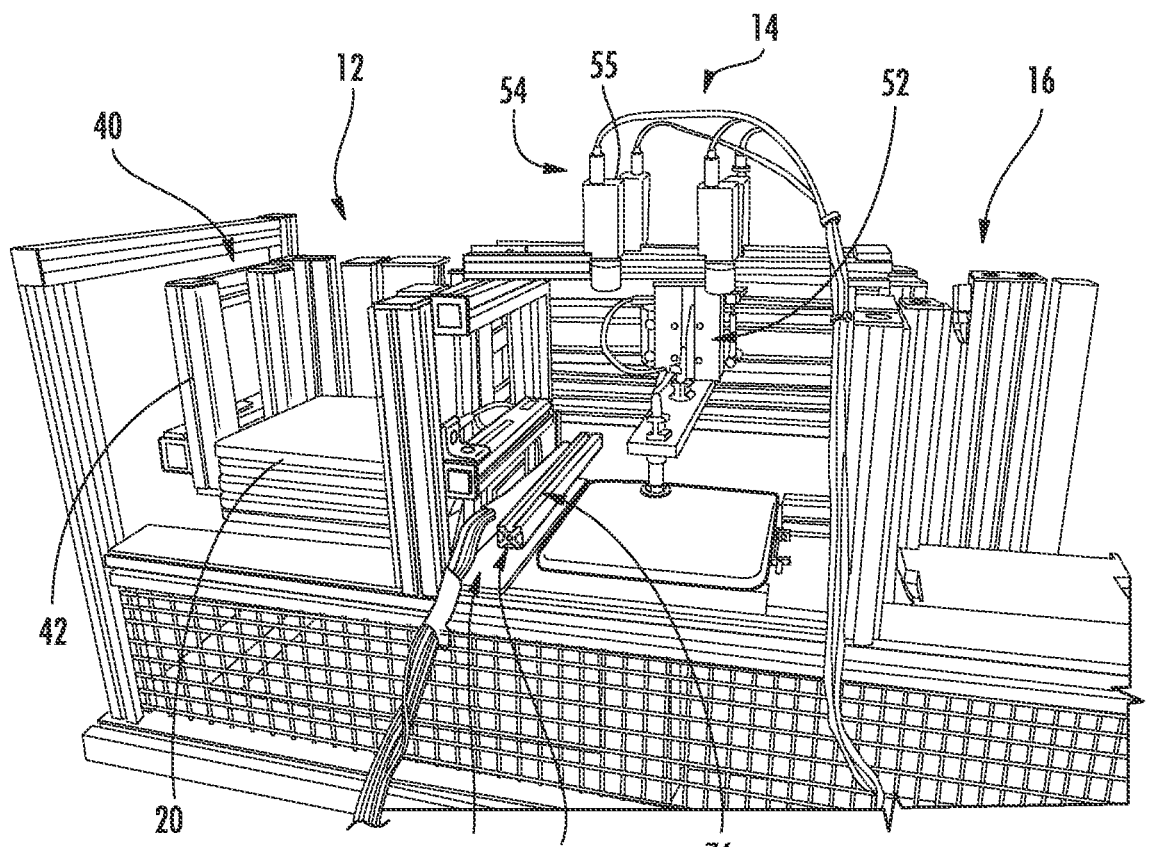
FIG. 5 is another perspective view of the plant tissue production apparatus of FIG. 1.

Referring to FIG. 5, input station 12 is shown according to an exemplary embodiment. Input station 12 includes a first rack system 40 configured to support a plurality of culture vessels 20 in an arranged (e.g., organized, etc.) manner before being presented to operational station 14. According to the embodiment illustrated, culture vessels 20 are arranged in a substantially vertical direction at first rack system 40. In particular, culture vessels 20 are shown as being stacked with one culture vessel 20 being directly supported by another culture vessel 20. To facilitate the stacking arrangement of culture vessels 20, first rack system 40 includes one or more guide structures (e.g., a track system, etc.), shown as rails 42, extending in a substantially vertical direction. According to the embodiment illustrated, a single stack (e.g., batch, etc.) of culture vessels 20 is provided at input station 12. First rack system 40 is configured to hold between approximately ten and approximately fifteen culture vessels 20, but alternatively, may be configured to hold more or less culture vessels 20. Culture vessels 20, the configuration of which is detailed below, are preferably all of the same size or at least have the same size footprint so that first rack system 40 does not have to be reconfigured, but alternatively may be of varying sizes.

According to the embodiment illustrated, rails 42 are positioned along three sides of culture vessels 20 stacked at input station 12. In particular, rails 42 are shown as being positioned along a first or left side, a second or right side and a third or rear side of input station 12. Such an arrangement allows culture vessels 20 to be removed from and/or added to input station 12 from a fourth or front side of input station 12 while still providing suitable guidance for culture vessels 20.

According to an exemplary embodiment, culture vessels 20 are configured to move (e.g., slide, etc.) in a substantially vertical direction relative to rails 42 before being transported to another station within apparatus 10. During such movement, at least a portion of culture vessels 20 are likely to be in direct contact with one or more of rails 42. To reduce the amount of friction (e.g., sliding friction, etc.) existing between culture vessels 20 and rails 42, and/or or reduce the amount of wear on culture vessel 20, friction reducing members (e.g., bearing surfaces, etc.), shown as pads 44, are coupled to rails 42. Pads 44 may be formed of any of a variety of known or otherwise suitable materials including, but not limited to, plastic (e.g., Delrin, etc.).

Figure 6:
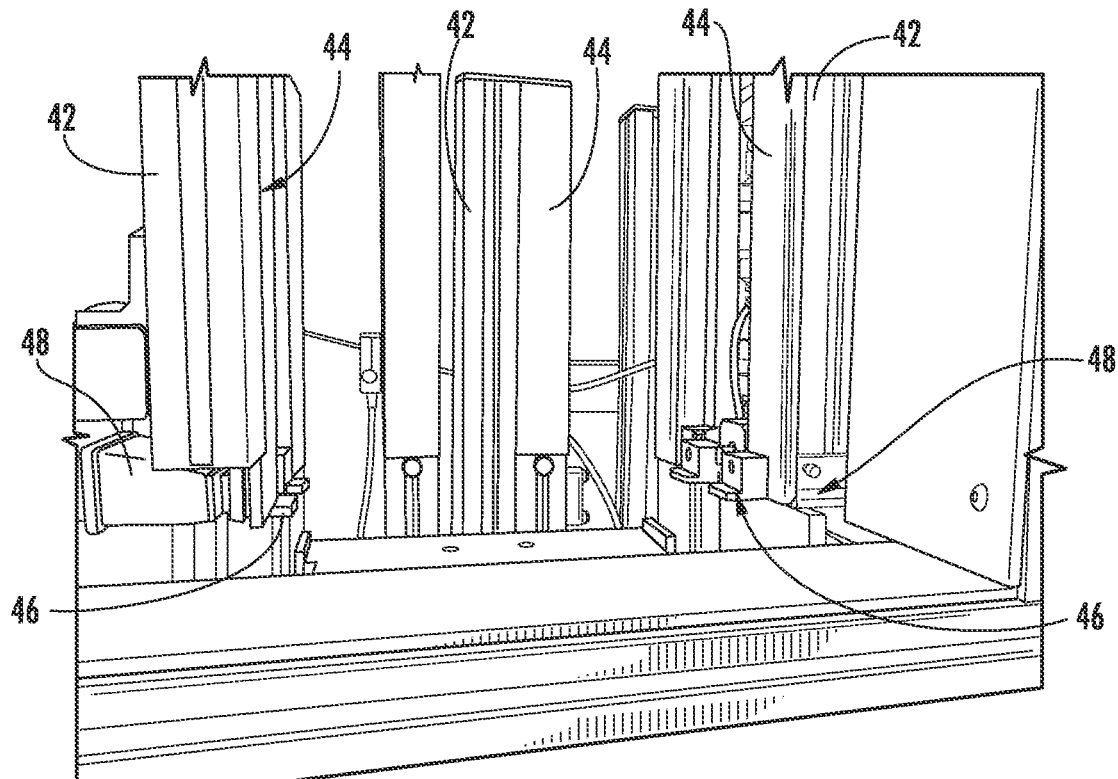
FIG. 6 is a perspective view of a first station of the plant tissue production apparatus shown according to an exemplary embodiment.

Referring to FIG. 6, culture vessels 20 arranged at input station 12 are supported in a horizontal plane by one or more support members (e.g., fingers, tabs, projections, etc.), shown as carriers 46. Carriers 46 are shown as being provided along the left and right sides of input station 12 and are configured to engage a bottom and/or side portion of the lowermost culture vessel 20 provided in the stack. According to the embodiment illustrated, two carriers 46 are provided along each of the left and right sides of input station 12. Carriers 46 are movable between a first or extended position and a second or retracted position to allow culture vessels 20 to move to another station within apparatus 10. In the extended position, carriers 46 support the entire stack of culture vessels provided at input station 12 by engaging the lowermost culture vessel 20 provided in stack. In the retracted position, carriers 46 release the lowermost culture vessel 20 by moving outward from culture vessels 20 in a substantially horizontal direction. As detailed below, when carriers 46 are in the retracted position, another mechanism (e.g., a component of transport system 18, etc.) is provided at input station 12 to support the stack of culture vessels 20.

To facilitate the movement of carriers 46 between the extended position and the retracted position, one or more movement devices (e.g., actuators, motors, drives, etc.), shown as linear actuators 48, are provided. According to an exemplary embodiment, a separate linear actuator 48 is associated with each carrier 46. Each linear actuator 48 is coupled to a controller (detailed below) so that the sequence of movement of culture vessels 20 between stations can be optimized. According to the various alternative embodiments, a single movement device may be provided at each side of input station 12 to control the movement of carriers 46 provided along that side.

One or more sensors can be provided at first rack system 40 to monitor the number of culture vessels 20 stacked within rails 42. The one or more sensors can be any type of detection sensor known or otherwise suitable and can be coupled to rails 42. For example, the one or more sensors can be capacitive, ultrasonic, optical or electrical-contacting sensors. If the one or more sensors detected that the number of incubations vessels 20 are low or depleted, one or more of the following actions can be taken: 1) the operation being conducted at operational station 14 can be halted; 2) additional culture vessels 20 can be delivered to first rack system 40; or 3) a warning may be generated via an alarm or display to warn an operator that the number of culture vessels 20 are low or depleted.

The delivery of culture vessels 20 to first rack system 40 may be done either manually (e.g., hand delivery, etc.) or via an automated delivery process. Culture vessels 20 may be delivered to first rack system 40 individually or as a batch (e.g., set, etc.) of culture vessels 20. For example, a batch of culture vessels 20 may be taken from a growth or development room (or any other area) and brought to apparatus 10. As indicated above, culture vessels 20 may be loaded from the front side of input station 12, or alternatively, may be loaded from the top of input station 12.

Referring to FIGS. 5 and 8-10, operational station 14 is shown according to an exemplary embodiment. Operational station 14 constitutes the area on apparatus 10 at which culture vessels 20 and/or the contents therein are acted upon (e.g., plated, analyzed, inspected, opened, sorted, collected, etc.). Provided at operational station 14 is a dispensing system 50, a manipulation system 52 and an imaging system 54. According to an exemplary embodiment, dispensing system 50 and manipulation system 52 are supported by one or more positioning devices or robots to provide for an at least partially automated system. According to the various alternative embodiments, one or more of dispensing system 50 and manipulation system 52 may be supported at a relatively fixed or stationary structure (e.g., support frame, housing, etc.).

Figure 8:
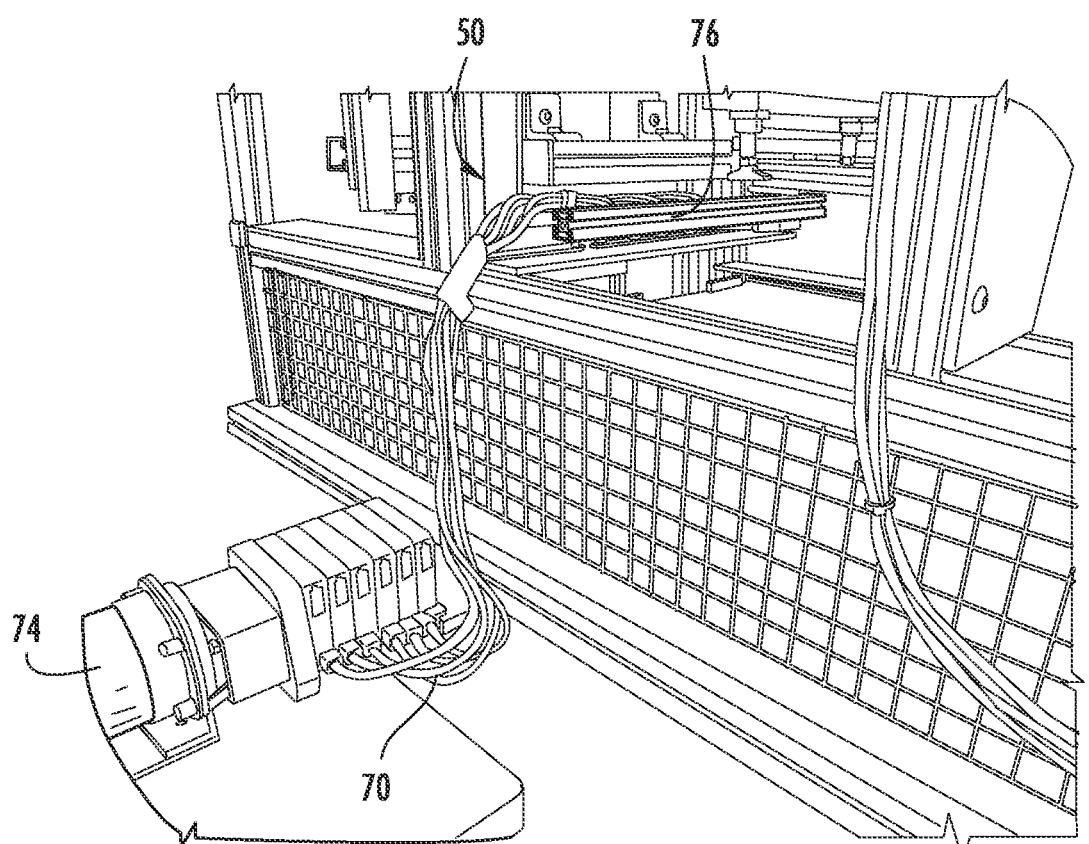
FIG. 8 is a perspective view of a second station of the plant tissue production apparatus shown according to an exemplary embodiment.
Figure 9:
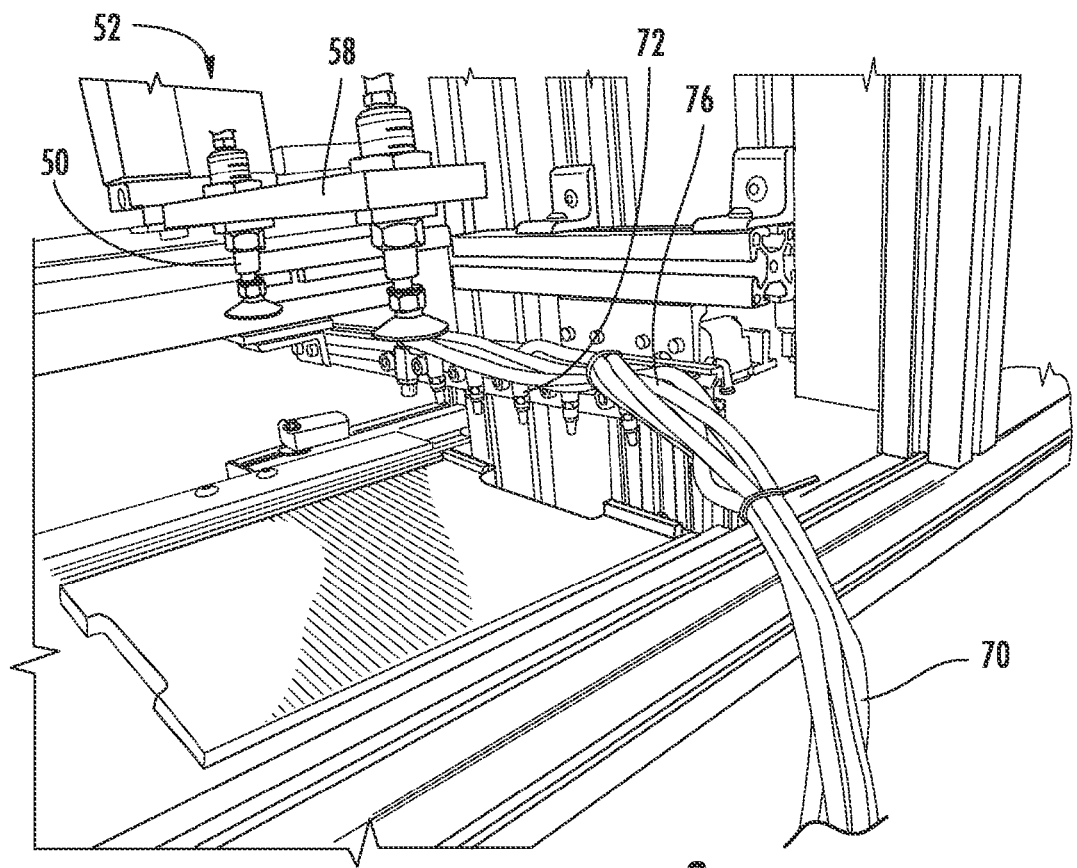
FIG. 9 is another perspective view of the second station of FIG. 8.

Referring to FIGS. 8 and 9 in particular, dispensing system 50 is shown according to an exemplary embodiment. Dispensing system 50 is configured to dispense a substance into an culture vessel 20 provided at operational station 14. According to an exemplary embodiment, dispensing system 50 is configured to dispense a base media into culture vessel 20 during one step in the production process and to dispense a plant tissue (e.g., embryogenic tissue, etc.) into culture vessel 20 during another step in the production process. Dispensing system 50 generally includes a housing (e.g., container, chamber, collection device, etc.), referred to broadly herein as a reservoir 71 (shown in FIG. 17), for holding the substance to be dispensed, one or more outlets (e.g., outputs, etc.), shown as nozzles 72, for directionally dispensing the substance, a pump 74 for moving the substance from reservoir 71 to nozzles 72, a support structure, shown as a robotic arm 76, for supporting and/or moving nozzles 72, and a conduit system 70 for providing fluid communication between reservoir 71, pump 74 and nozzles 72.

Figure 17:
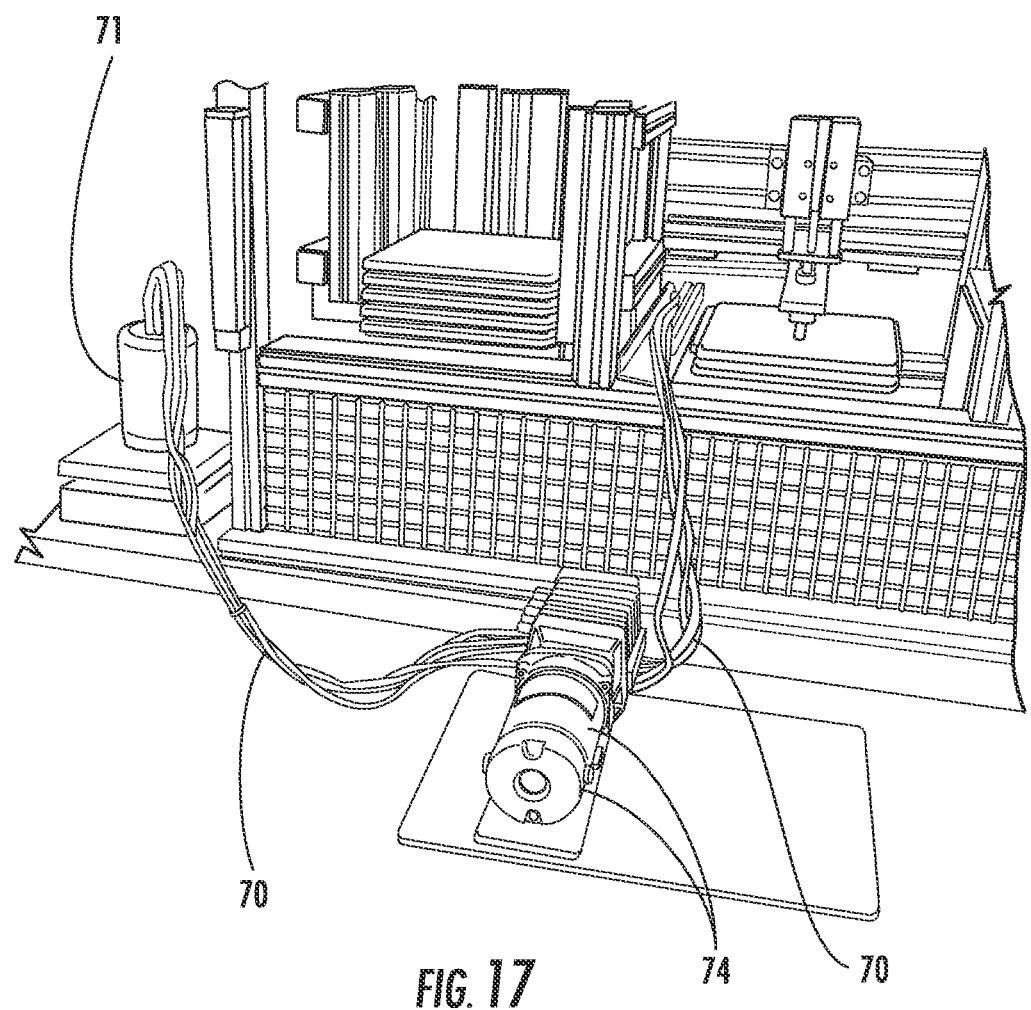
FIG. 17 is another perspective view of the plant tissue production apparatus of FIG. 1 showing a reservoir according to an exemplary embodiment.

Referring to FIG. 17, reservoir 71 can be used to hold or otherwise contain a substance that will ultimately exit through nozzles 72. Reservoir 71 may be positioned at apparatus 10, or alternatively, may be positioned at a remote location relative to apparatus 10 and have a conduit system communicating between the reservoir and apparatus 10. According to the embodiment illustrated, reservoir 71 includes a single container (e.g., bottle, beaker, etc.) defining a receptacle for containing a substance to be dispersed from nozzles 72. According to the various alternative embodiments, the reservoir may include any number of containers defining receptacles for containing substances to be dispersed from nozzles 72. The multiple containers may contain the same substance, or alternatively, may be used to hold different substances that can be mixed and/or used independently of the other substances. According to further alternative embodiments, the reservoir may be divided into separate compartments so that a single reservoir can hold different substances simultaneously. Reservoir 71 is a modular system configured to be interchanged with a second reservoir depending upon the particular operation being conducted at operational station 14 and/or when a first reservoir is emptied and/or when a reservoir is no longer needed within apparatus 10.

Reservoir 71 is shown as being substantially transparent so that an operator can see through and monitor or observe the substance contained therein. Reservoir 71 may be formed of any of a number of materials including, but not limited to, a clear polycarbonate, transparent glass, or other type of transparent material. Reservoir 71 can be any shape, such as cylindrical, pyramidal, conical, or cubical. Further, one or more sensors can be used to monitor the substance level within reservoir 71 and to send a signal to the controller (detailed below) that the controller may use to cause a particular action to take place (e.g., stopping of the operation, refilling of reservoir 71, generation of an alarm or an informational display, etc.).

As indicated above, dispensing system 50 may be used in plating an embryogenic tissue into culture vessel 20. In certain situations, it is desirable to "bulk-up" embryogenic tissue before transferring it onto an embryo development media. For example, embryogenic tissue cultures that have been cryogenically-stored, for instance, are plated onto gelled medium and incubated for a period of time until there is sufficient growth to justify their transfer to a development medium.

The embryogenic tissue may also be "bulked-up" or grown in a liquid version of the traditional gel medium. Eliminating the plating step may help to streamline the embryo development process and reduce costs associated with making the gel plates. For this liquid version, liquid suspension cultures are established by initially dispersing embryogenic tissue in liquid media in an appropriately sized flask or bioreactor. Additional liquid suspension medium can be routinely added during the incubation period. Cultures can be monitored until they have grown to a mass that is suitable for plating for embryo development.

Embryogenic tissues that have been bulked up from either the traditional gel or the alternative liquid suspension media can be used to develop somatic embryos. An amount of the bulked up tissue can be transferred to culture vessel 20 and placed onto the surface of embryo development medium. For the liquid version, or in any other application in which it may be desirable, the flask or bioreactor itself may be coupled to or used as reservoir 71 of dispensing system 50.

Referring to FIG. 9 in particular, nozzles 72 are shown according to an exemplary embodiment. Nozzles 72 constitute the exit for the substance contained within the reservoir before it is applied in culture vessels 20. According to the embodiment illustrated, dispensing system 50 is shown as having a plurality of nozzles 72 supported by robotic arm 76. In particular, nozzles 72 are shown as being spaced apart from each other in a generally linear manner along robotic arm 76 and are generally fixed relative thereto. Nozzles 72 cooperate to span a distance that is substantially equal to at least one dimension of culture vessel 20 (e.g., the depth of culture vessel 20, etc.) so that a substance can be equally applied to the entire culture vessel 20 if desired.

The number and configuration of nozzles 72 used at operational station 14 can be selected depending upon the desired flow rate and/or lay down (e.g., spray, etc.) pattern of the substance. For example, the velocity or pressure of the substance exiting nozzles 72 may be selected such that a consistent layer of the substance is applied to culture vessel 20. The velocity of the fluid is dependent upon the line pressure and the design of the nozzles. The velocity or pressure of the substance can be changed for different types of substances by simply changing the nozzles. It should be noted that substance (e.g., suspension, etc.) being dispersed from nozzles 72 may be a relatively viscous substance (e.g., gel-like, etc.) or a relatively thin substance (e.g., runny, diluted, etc.).

The selection of nozzles 72 also can be based on the desired lay down pattern of dispensing system 50. For example, if the substance being dispersed from nozzles 72 is a relatively viscous substance, nozzles 72 may selected for their ability to lay down relatively continuous rows of the substance. Alternatively, if the substance being dispersed from nozzles 72 is a relatively thin substance (thereby resulting in a spray), a conical spray pattern may be desired in which the spray impinging on culture vessel 20 and/or base media contained therein has an even distribution. Alternatively, the spray pattern may be in a more annular pattern in which more of the relatively thin substance is directed toward the center of the spray while there is less substance around the spray's periphery. One with ordinary skill in the art, once made aware of this disclosure, can determine suitable nozzles based on the desired lay down pattern and the line pressure.

It should be noted that while the embodiment illustrated shows the use of multiple nozzles, according to the various alternative embodiments, a single nozzle may be used. Such a nozzle may be supported by a fixed or movable structure depending on the application and may have any of a variety of configurations.

Referring back to FIGS. 8 and 17 in particular, pump 74 is shown according to an exemplary embodiment. Pump 74 is coupled between reservoir 71 and nozzles 72 and is configured to transfer the substance contained with reservoir 71 to nozzles 72 for distribution to culture vessel 20. According to an exemplary, pump 74 is a peristaltic pump having a pump speed of between approximately 100 and approximately 600 revolutions per minute. For example, pump 74 may have a pump speed of approximately 270 revolutions per minute. According to the various alternative embodiments, pump 74 may be selected to have any of a variety of performance capabilities depending on the particular application.

Still referring to FIGS. 8 and 17, conduit system 70 is shown according to an exemplary embodiment. Conduit system 70 includes suitable plumbing (e.g., tubing, piping, valves, etc.) provided at an input side of pump 74 and at an output side of pump 74 for communicating with reservoir 71 and nozzles 72 respectively. According to the embodiment illustrated, separate tubing is provided between reservoir 71 and pump 74 and between pump 74 and each nozzle 72. According to the various alternative embodiments, one or more tubes may be coupled to a manifold system in fluid communication with nozzles 72. Such a manifold system may be supported at robotic arm 76. According to an exemplary embodiment, the tubing used between reservoir 71 and the input of pump 74 and between the output of pump 74 and nozzles 72 has an inside diameter between approximately 0.06 inches and approximately 0.31 inches. For example, the tubing between reservoir 71 and the input of pump 74 and between the output of pump 74 and nozzle 72 may have an inside diameter of approximately 0.12 inches. According to the various alternative embodiments, tubing of any size may be used depending on the particular application.

Referring to FIGS. 5 and 8, robotic arm 76 is shown according an exemplary embodiment. Robotic arm 76 is configured to support nozzles 72 in a movable manner relative an culture vessel 20 provided at operational station 14. According to the embodiment illustrated, robotic arm 76 is a substantially rectangular member extending outward in a direction that is substantially perpendicular to the length of apparatus 10 (i.e., robotic arm 76 extends outward in a direction that is substantially parallel to a Y-axis of apparatus 10). Robotic arm 76 is configured to move from side-to-side while remaining in substantially the same horizontal plane. To facilitate the movement of robotic arm 76, one or more movement devices (e.g., actuators, motors, etc.) is provided. In particular, a linear actuator (not shown) is coupled to a rear portion of robotic arm 76 to selectively move robotic arm 76 from side-to-side (i.e., along the width of operational station 14). The linear actuator is coupled to a controller (detailed below) so that its movement can be at least partially automated. According to the various alternative embodiments, robotic arm 76 may 3-degrees-of-freedom (i.e., movement in an X-direction, Y-direction and Z-direction) for moving nozzles 72 in a variety of directions. According to further alternative embodiments, robotic arm 76 may up to 6-degrees-of-freedom (i.e., movement in an X-direction, Y-direction and Z-direction, plus rotational movement in three axes for complete maneuverability of nozzles 72 or any other device supported by robotic arm 76 (e.g., embryo manipulators, etc.)).

When operational station 14 of apparatus 10 is not being used for dispensing a substance, robotic arm 76 is moved to a storage position, which may be located at a periphery of operational station 14 (e.g., the left side, etc.), to avoid the possibility of interfering with another step that may later occur at operational station 14 (e.g., an inspection of culture vessels 20 using imaging system 54, etc.). Since nozzles 72 may continue to dispense (e.g., leak, drip, etc.) a substance while robotic arm 76 is in the storage position, a collection device (e.g., tray, reservoir, etc.), shown in FIG. 5 as a drip plate 59, is provided under nozzles 72 to collect any substance being discharged. Drip plate 59 preferably retains any such substance and/or directs it so that the substance does not contaminate and/or damage other components of apparatus 10.

Figure 10:
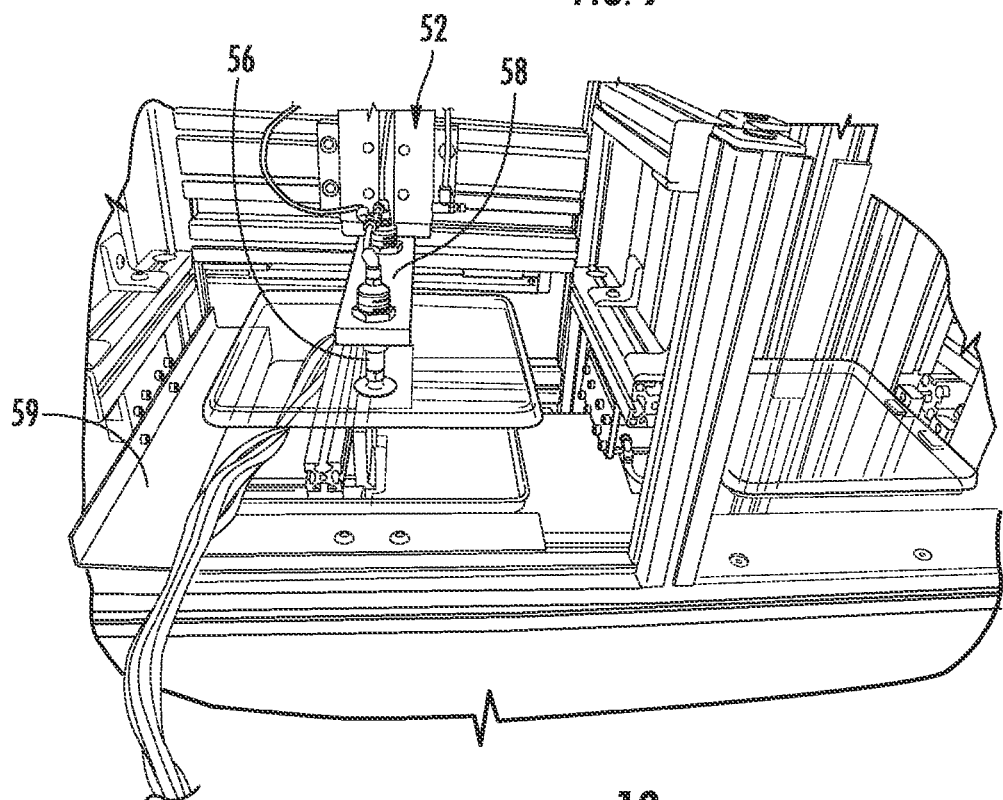
FIG. 10 is another perspective view of the second station of FIG. 8.

Referring to FIGS. 9 and 10, manipulation system 52 is shown according to an exemplary embodiment. Manipulation system 52 is configured to engage an culture vessel 20 provided at operational station 14 to move the culture vessel 20 between an opened position and a closed position. Manipulation system 52 includes one or more operating tools coupled to a support structure, shown as a robotic arm 58, for engaging culture vessels 20. According to the embodiment illustrated, the one or more operating tools include a pair of vacuum heads 56 coupled to a vacuum system. Relying upon a negative pressure differential generated by the vacuum system, vacuum heads 56 are configured to engage and hold a cover portion of culture vessel 20 away from a base portion of culture vessel 20 while culture vessel 20 is undergoing an operation at operational station 14. According to the various alternative embodiments, vacuum heads 56 may be replaced with any other tool suitable for moving culture vessels 20 between the opened and closed positions (e.g., a gripping device, etc.).

According to the embodiment illustrated, robotic arm 58 is configured to move in a substantially vertical direction so that vacuum heads 56 can engage and move the cover portion of culture vessel 20 relative to the base portion. To facilitate the movement of robotic arm 58, one or more movement devices (e.g., actuators, motors, etc.) is provided. In particular, a linear actuator 53 is coupled to a rear portion of robotic arm 58 to selectively move robotic arm 58 in a substantially vertical direction (i.e., up and down). Linear actuator 53 is coupled to a controller (detailed below) so that its movement can be at least partially automated.

According to the various alternative embodiments, manipulation system 52 may also include one or more additional robotic arms having operating tools for manipulating the contents of an culture vessel 20 provided at operational station 14 after being opened by robotic arm 58. These additional robotic arms may be configured to selectively perform at least one of the following operations: 1) place a plant tissue onto culture vessel 20; and/or 2) collect plant tissue (e.g., somatic embryos, etc.) from culture vessel 20. The operating tools of these additional robotic arms may include a gripping device (e.g., a claw, tweezers, etc.), a suction device (e.g., coupled to a vacuum system, etc.), or any other known or otherwise suitable device for performing any one of the operations just mentioned.

Such robotic arms may include an operating head configured to support a plurality of operating tools. One or more of the operating tools supported at the operating head can be interchangeable so that apparatus 10 can be reconfigured (e.g., retooled, etc.) for different steps in the plant embryo production process. The operating tools can be used alone or in combination with another tool supported at the operating head (e.g., a camera of an imaging system, etc.). The robotic arm and/or the operating head may have up to 6-degrees-of-freedom (i.e., movement in an X-direction, Y-direction and Z-direction, plus rotational movement in three axes for complete maneuverability of embryo manipulation or operating tools). To facilitate the desired movement of the robotic arm and/or the operating head, a first linear actuator (i.e., X-direction linear actuator), a second linear actuator (i.e., Y-direction linear actuator) and a third linear actuator (i.e., Z-direction linear actuator) may be provided along with actuators (e.g., servo motors, etc.) that provide rotational movement.

Each linear actuator may be driven by a separate motor (e.g., a servo motor, etc.) that provides for the linear motion of the robotic arm and/or the operating head along its respective axis. Each linear actuator may also include a guide (e.g., rail, shaft, etc.) to provide for its linear movement. The first linear actuator may selectively move the operating head side-to-side (e.g., right and left, etc.) or along the X-axis of apparatus 10. The second linear actuator may selectively move the operating head in-and-out (e.g., front to back, etc.) or along the Y-axis of apparatus 10. The third linear actuator may selectively move the operating head up-and-down or along the Z-axis of apparatus 10. To provide rotational movement for the robotic arm and/or operating head, the system may include a combination of polar axes driven by servo motors. The actuators (both linear and rotational) may be operated separate from the other actuators or simultaneously with one or more of the other actuators.

Referring back to FIG. 5, imaging system 54 is shown according to an exemplary embodiment. Imaging system 54 is configured to obtain images of the contents of an culture vessel 20 (e.g., plant tissue, such as somatic embryos, etc.). According to an exemplary embodiment, imaging system 54 includes one or more cameras 55 (e.g., digital imaging cameras, charged coupled devices (CCD), etc.) supported above the position of an culture vessel 20 provided at operational station 14. While only a single camera may be used, use of additional cameras may improve the resolution of the inspection. According to the embodiment illustrated, imaging system 54 includes four cameras 55. Each camera 55 is provided to obtain an image of approximately one fourth of an culture vessel 20 (e.g., one quadrant, etc.) provided at operational station 14 and is fixedly coupled to a support member 57 extending laterally across operational station 14. Cameras 55 may be operatively coupled to a display screen, a controller (detailed below) and/or suitable image processing software.

Imaging system 54 may be used to obtain any of a number of characteristics of the plant tissue including, but not limited to, size, shape, development, symmetry, color, quantity, etc. By obtaining images of the characteristics, imaging system 54 may be useful in the steps of plant embryo inspection, embryo quality assessment and/or embryo sorting. During inspection, the images of the plant embryos may be stored in a database system so that their development can be tracked through several stages of the production process. When its desirable to make a quality assessment of each plant embryo, the image processing software may be used to make such a determination. The image processing software is able to make a qualitative decision as to whether each plant embryo is to be considered "quality" or "non-quality" based upon predetermined parameters of one or more characteristics of the plant embryos. Based upon the quality assessment determined by the image processing software, the controller may direct one or more of the robotic arms of manipulation system 52 to act accordingly (e.g., to collect only those plant embryo determined to be quality, etc.).

In addition to imaging system 54, apparatus 10 may include additional inspection systems intended to monitor development within culture vessels 20. For example, apparatus 10 may include inspection systems configured to inspect chemical properties within the vessels (e.g., pH, etc.), media properties (e.g., depth, etc.) and/or any other properties that may be desirable to inspect.

Figure 7:
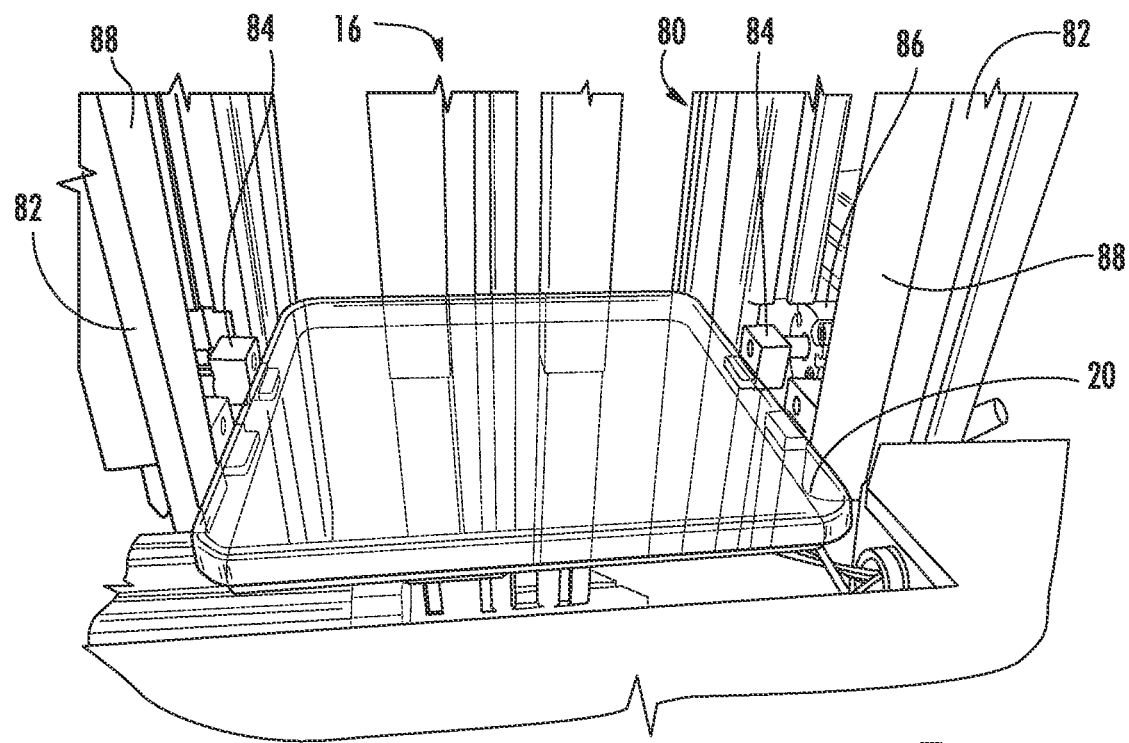
FIG. 7 is a perspective view of a third station of the plant tissue production apparatus shown according to an exemplary embodiment.

Referring to FIG. 7, apparatus 10 further includes output station 16. Output station 16 is shown as having a second rack system 80 configured to support a plurality of culture vessels 20 in an arranged manner after passing through operational station 14. According to an exemplary embodiment, the configuration of second rack system 80 is substantially similar to the configuration of first rack system 40. As such, culture vessels 20 are arranged (e.g., stacked, etc.) in a substantially vertical direction at second rack system 80 with one culture vessel 20 being directly supported by another culture vessel 20. Second rack system 80 also includes one or more guide structures (e.g., track system, etc.), shown as rails 82, extending in a substantially vertical direction. Like first rack system 40, second rack system 80 is configured to hold up to between approximately ten and approximately fifteen culture vessels 20, but alternatively, may be configured to hold more or less culture vessels 20.

According to an exemplary embodiment, culture vessels 20 are configured to move (e.g., slide, etc.) in a substantially vertical direction relative to rails 82 when additional culture vessels 20 are added to output station 16 from operational station 14. During such movement, at least a portion of culture vessels 20 are likely to be in direct contact with one or more of rails 82. To reduce the amount of friction (e.g., sliding friction, etc.) existing between culture vessels 20 and rails 82, and/or or reduce the amount of wear on culture vessel 20, friction reducing members (e.g., bearing surfaces, etc.), shown as pads 84, are coupled to rails 82. Pads 84 may be formed of any of a variety of known or otherwise suitable materials including, but not limited to, plastic (e.g., Delrin, etc.).

Similar to input station 12, culture vessels 20 arranged at output station 16 are supported in a horizontal plane by one or more support members (e.g., fingers, tabs, projections, etc.), shown as carriers 86. Carriers 86 are shown as being provided along the left and right sides of output station 16 and are configured to engage a bottom and/or side portion of the lowermost culture vessel 20 provided in the stack. According to the embodiment illustrated, two carriers 86 are provided along each of the left and right sides of output station 16. Carriers 86 are movable between a first or extended position and a second or retracted position to allow output station 16 to receive additional culture vessels 20 from operational station 14. In the extended position, carriers 86 support the entire stack of culture vessels 20 provided at output station 12 by engaging the lowermost culture vessel 20 provided in stack. In the retracted position, carriers 86 release the lowermost culture vessel 20 by moving outward from culture vessels 20 in a substantially horizontal direction (i.e., the Y-axis of apparatus 10). As detailed below, when carriers 86 are in the retracted position another mechanism (e.g., a component of transport system 18, etc.) is provided at output station 12 to support the stack of culture vessels 20.

To facilitate the movement of carriers 86 between the extended position and the retracted position, one or more movement devices (e.g., actuators, motors, etc.), shown as linear actuators 88, are provided. According to an exemplary embodiment, a separate linear actuator 88 is associated with each carrier 86. Each linear actuator 88 is coupled to a controller (detailed below) so that the sequence of movement of culture vessels 20 between stations can be optimized. According to the various alternative embodiments, a single movement device may be provided along each side of input station 12 to control the movement of carriers 86 provided along that side.

One or more sensors can be provided at second rack system 80 to monitor the number of culture vessels 20 stacked within rails 82. The one or more sensors can be any type of detection sensor known or otherwise suitable and can be coupled to rails 82. For example, the one or more sensors can be capacitive, ultrasonic, optical or electrical-contacting sensors. If the one or more sensors detected that the number of incubations vessels 20 are low or depleted, one or more of the following actions can be taken: 1) the operation being conducted at operational station 14 can be halted; 2) culture vessels 20 can be removed from second rack system 80; or 3) a warning may be generated via an alarm or display to warn an operator that the number of culture vessels 20 is high or at its limit.

The removal of culture vessels 20 to first rack system 40 may be done either manually (e.g., hand delivery, etc.) or via an automated delivery process. Culture vessels 20 may be removed from first rack system 40 individually or as a batch (e.g., set, etc.) of culture vessels 20. For example, a batch of culture vessels 20 may be removed from second rack system 80 after undergoing an operation at operational station 14 (e.g., tissue plating, etc.) and taken to a growth or development room for an extended period of time. Due to the configuration rails 82, culture vessels 20 may be removed from the front of output station 16 and/or the top. As detailed, above an identification device may be provided on culture vessels 20 that be used to track the progress of the contents of the culture vessels and/or may be used by an automated delivery or warehousing system.

To facilitate the movement of culture vessels 20 between input station 12, operational station 14 and output station 16, transport system 18 is provided. According to an exemplary embodiment, transport system 18 is configured to de-stack an culture vessel 20 supported at input station 12, move the de-stacked culture vessel 20 from input station 12 to operational station 14, move the culture vessel 20 provided at operational station 14 to output station 16 and re-stack the culture vessel 20 coming from operational station 14 at output station 16. In an effort to avoid disrupting the development of the plant embryos, transport system 18 is configured to move culture vessels 20 in a substantially horizontal direction between input station 12, operational station 14 and output station 16. In a further effort to limit the disruption of the contents of culture vessel 20 during movement, culture vessels 20 are taken from the bottom of the stack at first rack system 40 and returned to the bottom of the stack at second rack system 80.

Referring to FIGS. 11A-11K, transport system 18 is shown according to an exemplary embodiment. Transport system 18 is shown as including a first vertical movement device (e.g., lift device, linear actuator, telescopic cylinder, etc.), shown as a first actuator 100, a second vertical movement device (e.g., lift device, linear actuator, telescopic cylinder, etc.), shown as a second actuator 102, a horizontal movement device (e.g., linear actuator, telescopic cylinder, conveyor, etc.), shown as an actuator 104, and a support structure 106 for coupling first actuator 100 and second actuator 102 to an operating portion of third actuator 104.

According to an exemplary embodiment, first actuator 100 is substantially similar to second actuator 102. First actuator 100 and second actuator 102 are configured to move in a substantially vertical direction to remove and/or present an culture vessel 20 from or to input station 12, operational station 14 and output station 16. First actuator 100 and second actuator 102 include a support member (e.g., platform, engaging device, etc.), shown as a lift plate 108 and 110 respectively, for supporting culture vessel 20.

First actuator 100 and second actuator 102 are also configured to move in a substantially horizontal direction (e.g., side-to-side, etc.). According to an exemplary embodiment, first actuator 100 is configured to be selectively moved in the horizontal direction between input station 12 and operational station 14, while second actuator 102 is configured to be selectively moved in the horizontal direction between operational station 14 and output station 16. The positioning of first actuator 100 relative to second actuator 102 in the horizontal direction remains constant due to support structure 106. First actuator 100 is spaced apart from second actuator 102 along support structure 106 so that first actuator 100 will be positioned at either input station 12 or operational station 14 when second actuator 102 is positioned at either operational station 14 or output station 16 respectively. According to the embodiment illustrated, support structure 106 includes a substantially linear member extending between a first end configured to support first actuator 100 and a second end configured to support second actuator 102. A bracket (e.g., plate, etc.) couples the linear member to third actuator 104 using one or more fastening techniques (e.g., one or more mechanical fasteners, such as bolts, rivets, screws, etc., a welding operation, etc.).

Figure 11A:
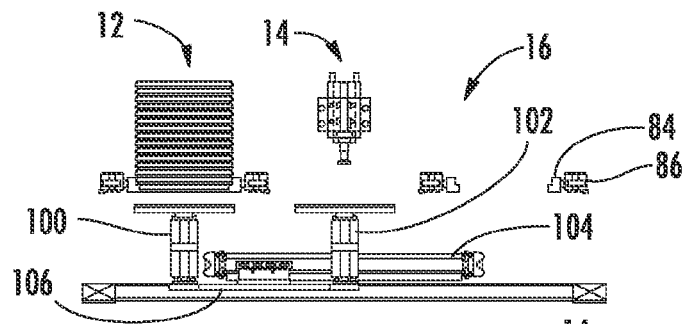
FIGS. 11A through 11K are schematics illustrating a transporting sequence of operation according to an exemplary embodiment.
Figure 11B:
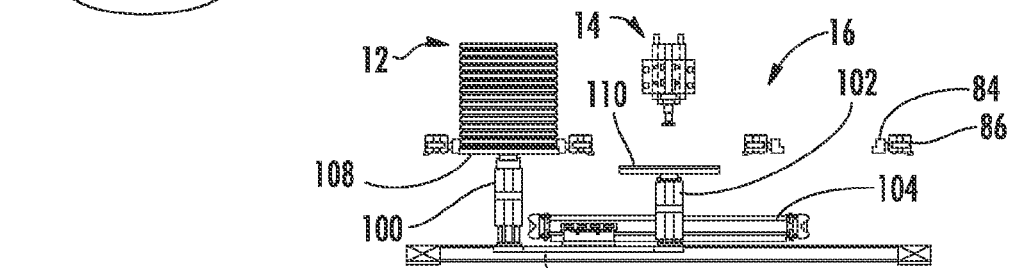
Figure 11C:
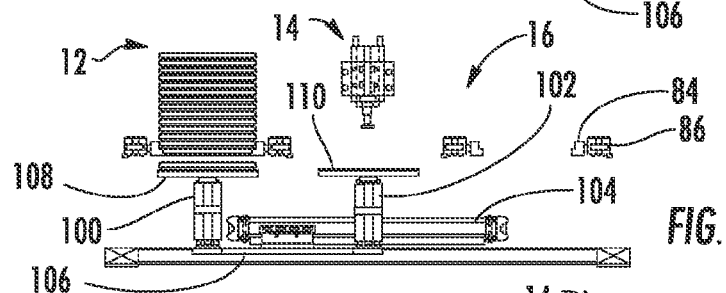
Figure 11D:
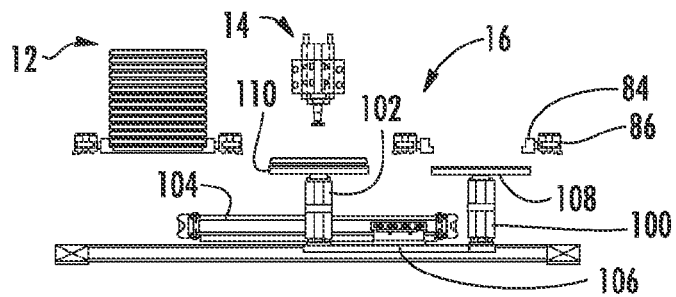

The method of moving an culture vessel 20 between input station 12, operational station 14 and output station 16 is sequentially shown in FIGS. 11A-11K. In FIG. 11A, all of culture vessels 20 are provided at input station 12, with first actuator 100 provided at input station 12 and second actuator 102 provided at operational station 14. In FIG. 11B, first actuator 100 is moved upwards in a vertical direction to engage the bottom of the lowermost culture vessel 20. Once engaged, carriers 46 are moved to the refracted position so that first actuator 100 is now supporting the entire stack of culture vessels 20. First actuator 100 then moves slightly downwards (e.g., a distance substantially equal to the depth of one culture vessel 20, etc.) and carriers 46 are moved back to the extended position to support the remaining stack of culture vessels 20. In FIG. 11C, first actuator 100 is moved downward to a retract position while supporting one culture vessel 20. In FIG. 11D, first actuator 100 and second actuator 102 are moved in a horizontal direction so that first actuator 100 is provided at operational station 14 and second actuator 102 is provided at output station 16.

Figure 11E:
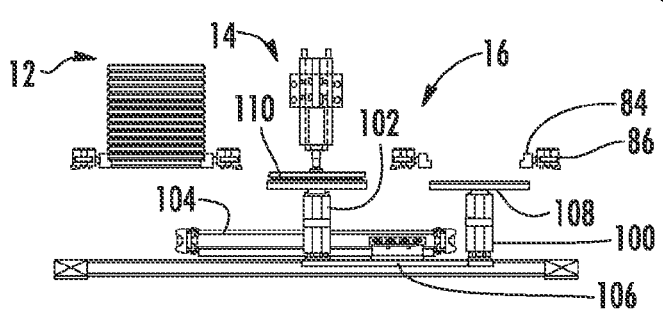
Figure 11F:
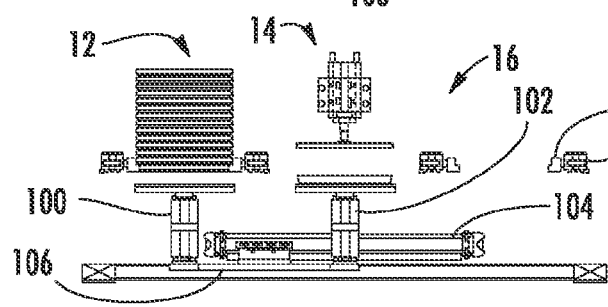
Figure 11G:
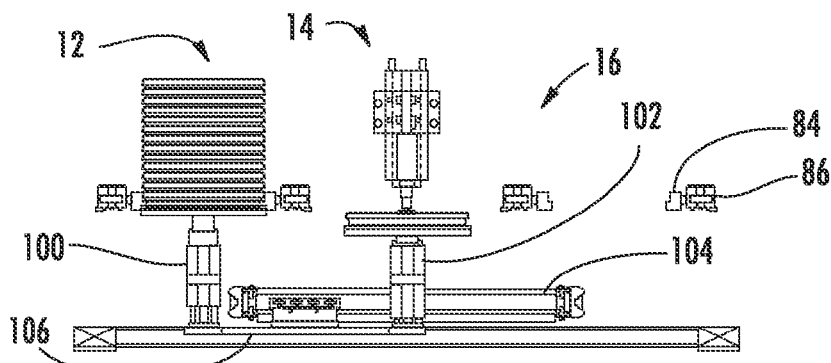
Figure 11H:
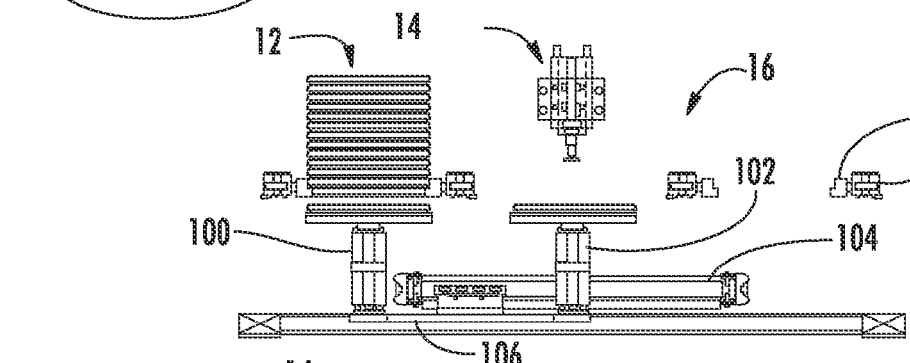
Figure 11I:
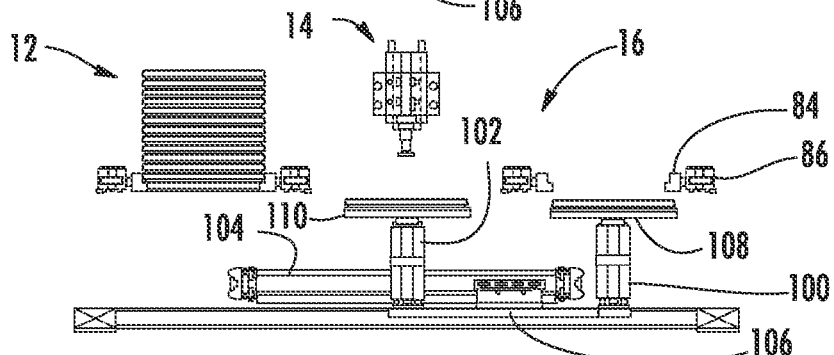
Figure 11J:
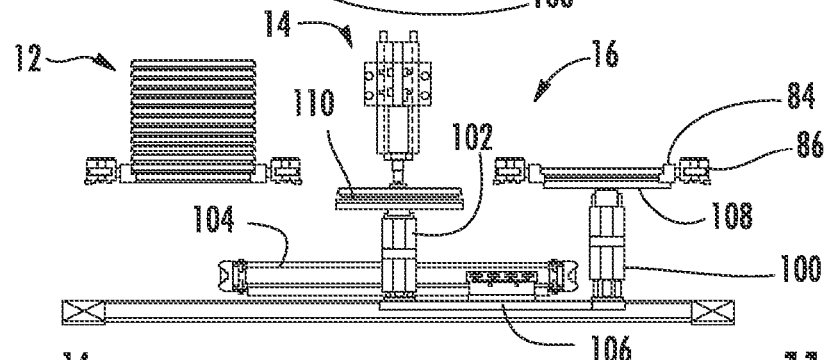
Figure 11K:
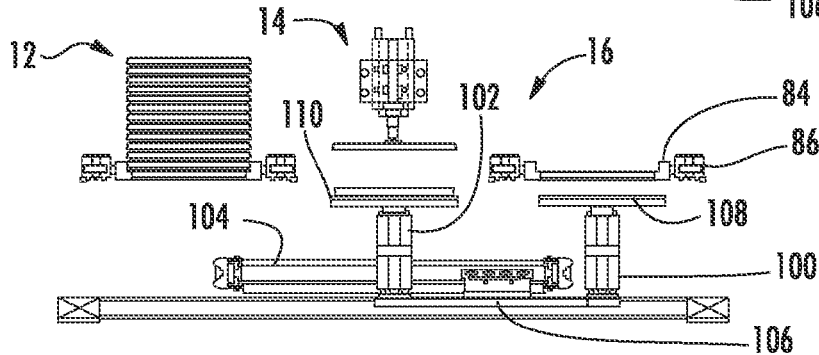

In FIG. 11E, the culture vessel 20 at operational station 14 is engaged and supported by manipulation system 52. First actuator 100 and second actuator 102 are then moved back in the horizontal direction so that first actuator 100 is once again provided at input station 12 and second actuator is provided at operational station 14 as shown in FIG. 11F. In FIGS. 11G and 11H, second actuator 102 now supports the first culture vessel 20 taken from input station 12 and first actuator 100 now supports a second culture vessel 20 taken from input station 12. In FIGS. 11I-11K, first actuator 100 and second actuator 102 are moved in the horizontal direction so that first actuator 100 is once again provided at operational station 14 and second actuator 102 is once again provided at output station 16. With second actuator 102 at output station 16, the first culture vessel 20 taken is re-stacked at output station 16 and supported by carriers 86. The process is repeated until all of the culture vessels 20 pass through operational station 14.

According to the various alternative embodiments, transport system 18 may include any of a number of known or otherwise suitable devices or components for moving culture vessels 20 between input station 12, operational station 14 and output station 16. According to another exemplary embodiment, transport system 18 may be configured to deliver culture vessels 20 to another operational system after passing through operational station 14. For example, transport system 18 may be configured to deliver culture vessels 20 to an automated mass harvesting system of the type discloses in U.S. Publication No. 2006/0260015 (referenced above). For such an embodiment, the mass harvesting system may be configured as a module that can be selectively added or removed from apparatus 10.

Apparatus 10 further includes a controller 90 for controlling at least one, and preferably all, of first rack system 40, second rack system 80, transport system 18, dispensing system 50, manipulation system 52 and imaging system 54, either automatically or by operator control. Controller 90 may be connected to and configured to control the components of these systems by one or more wire transmission lines extending between the various devices that it operates and to the sensors which send it information or by a wireless interface.

Controller 90 may comprise a display, one or more microprocessors, memories, input/output lines, a graphical user interface, and/or one or more operation buttons. Controller 90 can include, for example, a small Programmable Logic Controller (PLC) with an operator interface for operator inputs, operational parameters, error messages, and production reports. A PLC with more digital inputs and outputs or a PC-based computer can be used for a fully automated system. For example, the controller may contain data processing programs in one or more microprocessors for processing data related to the sensors and programs for performing operational commands for controlling, linear actuators 48, robotic arm 58, vacuum heads 56, cameras 55 and/or the various movement devices of transport system 18. Furthermore, the controller can be configured to control the output flow from nozzle 72 by controlling pump 74 and/or one or more valves or regulators associated therewith.

Controller 90 can be programmed to make an entire operation automatic from the time when a batch of culture vessels 20 are loaded at input station 12 to the time when they are removed from output station 16. Alternatively, controller 90 can be programmed to make only portions of an operation automatic. For example, the operation taking place at operational station 16 (e.g., plating, inspection, collecting, etc.) can be automated while the movement of culture vessels 20 between input station 12, operational station 14 and output station 16 are operator-controlled either manually (by hand)

or via the controller. Another example can be to have the entire operation automated while providing an operator with the option to halt the operation if desired. For example, if the operator wishes to have an culture vessel undergo an additional inspection operation, the operation can use the controller to halt the entire inspection operation and repeat the inspection operation.

Referring back to FIGS. 1 and 2, controller 90 is shown as including an ON/OFF switch 92, an interface 94, and a display 96. Display 96 may be part of interface 94 or may be a separate component. Interface 94 allows an operator to input parameters for the particular operation being performed. Interface 94 may be a graphical interface, a touch screen interface, a keyboard or any other known or otherwise suitable user interface. Display 96 may display operational variables and parameters to the operator. For example, in the case of an embryogenic tissue plating operation, the number of plating operations performed, the speed of pump 74, the flow rate at nozzle 72, any warnings regarding the sensors at first rack system 40 or second rack system 80, etc. can be shown on display 96. Further, if culture vessels 20 include an identification device, information stored thereon can be shown on display 96 and made available to an operator.

Figure 2:
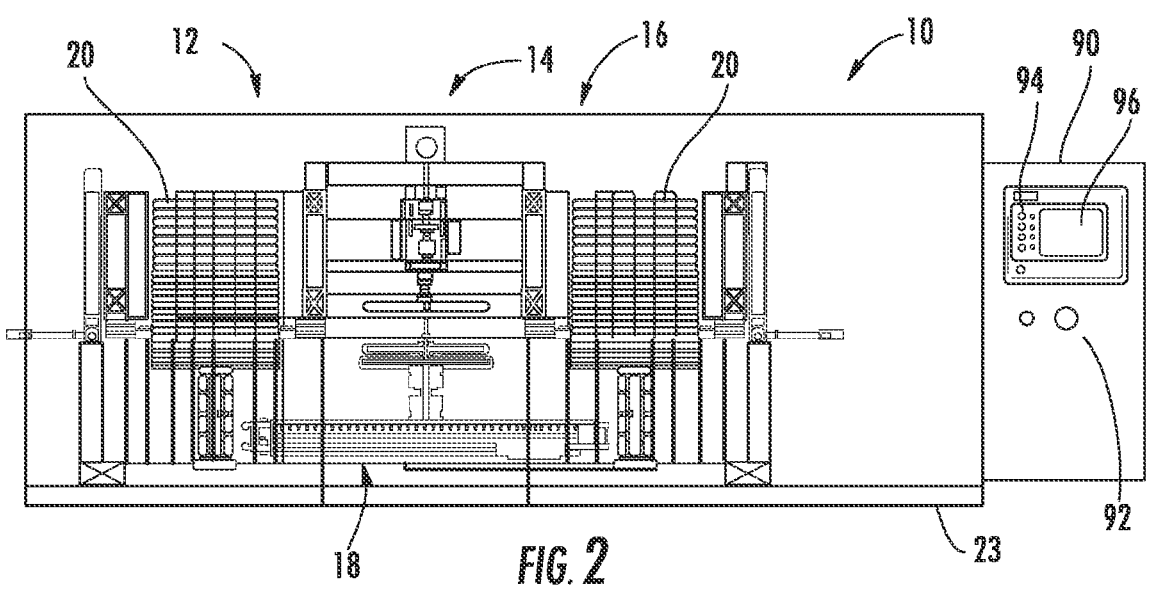
FIG. 2 is a front elevation view of the plant tissue production apparatus of FIG. 1.
Figure 3:
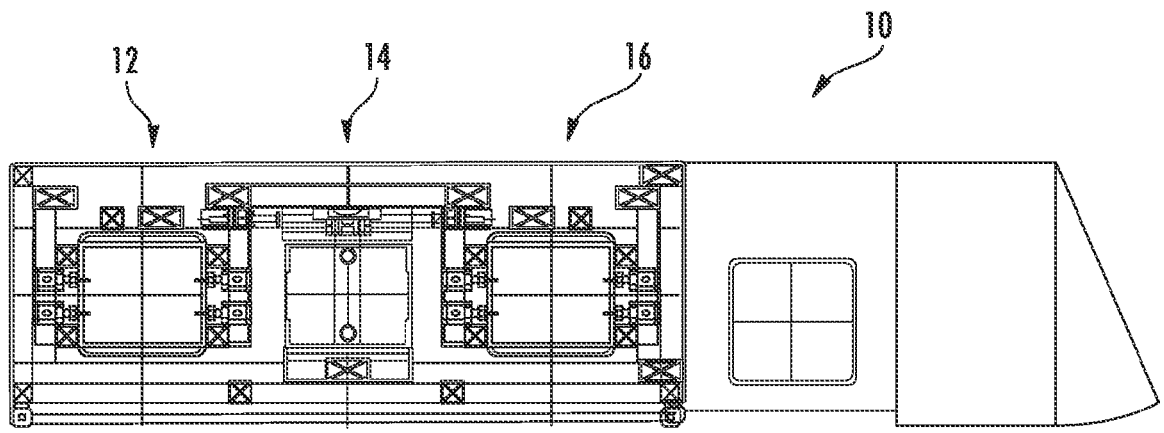
FIG. 3 is a top plan view of the plant tissue production apparatus of FIG. 1.
Figure 4:
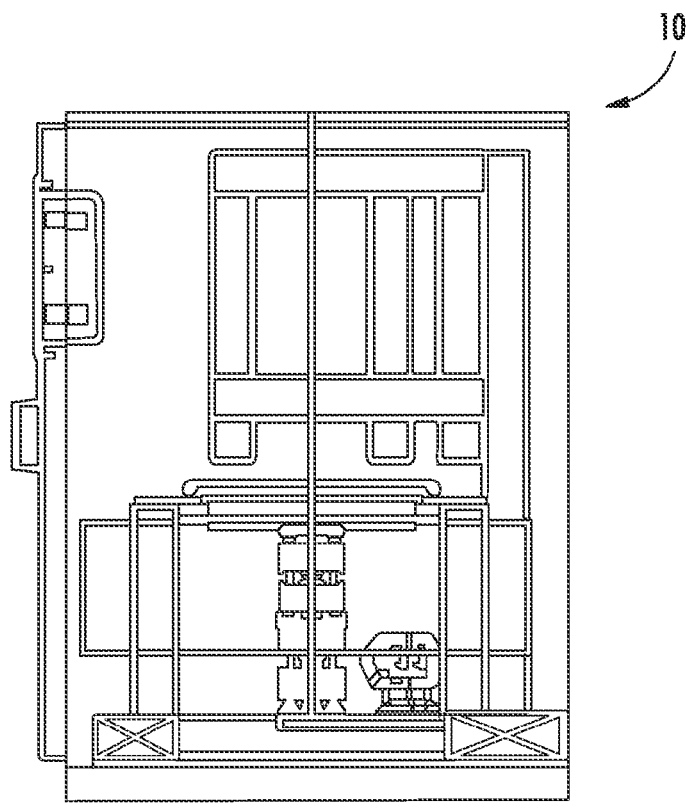
FIG. 4 is a side elevation view of the plant tissue production apparatus of FIG. 1.

Still referring to FIGS. 1 and 2, and according to an exemplary embodiment, input station 12, operational station 14, output station 16 and transport system 18 of apparatus 10 are provided within a relatively sterile or low contamination environment (e.g., a clean room, etc.). According to the embodiment illustrated, to facilitate a relatively sterile or low contamination environment for the plant embryos throughout the production process, input station 12, operational station 14, output station 16 and transport system 18 of production apparatus 10 are located within a relatively sterile enclosure (e.g., HEPA-filtered chamber, etc.), shown as a laminar flow hood 23. According to an exemplary embodiment, laminar flow hood 23 has a width that is approximately sixty inches, a depth that is approximately twenty inches and a height that is approximately twenty-eight inches. Providing the components of production apparatus 10 within laminar flow hood 23 reduces the likelihood that the plant embryos will be contaminated during the production process. In the case of use in a laminar flow hood, it is important to optimize the design and orientation of the components of the apparatus so as to minimize the redirection of air in the hood.

According to an exemplary embodiment wherein the components of apparatus 10 are enclosed within laminar flow hood 23, controller 90 is provided outside of laminar flow hood 23. Such positioning of controller 90 may advantageously allow an operator to access ON/OFF switch 92, interface 94, and/or display 96 of controller 90 without breaching the environment maintained within laminar flow hood 23 for the plant embryos. Further, such positioning of controller 90 may prolong the useful life of controller 90 by shielding the components of controller 90 (e.g., electronics, etc.) from an environment (e.g., relatively high humidity levels, etc.), that may adversely affect their continued operation.

It should be noted that input station 12, operational station 14, output station 16 and/or transport system 18 of apparatus 10 can be used effectively outside of a relatively sterile or low contamination environment. For example, certain applications may be less sensitive and may not require a relatively sterile or low contamination environment to achieve the results desired. In such applications, apparatus 10 may be set up in any location that is convenient.

Referring now to FIGS. 13-16, culture vessel 20 is shown according to an exemplary embodiment. Culture vessel 20 provides a structure suitable for supporting the development of plant tissue throughout various steps of the production process. For example, culture vessel 20 can be used for plating, inspection, quality assessment, growth, harvesting, conditioning, etc. Culture vessel 20 is designed to hold both liquid and solid substances. For example, culture vessel 20 is designed to hold a base media material, an embryogenic tissue and one or more developed plant embryos. According to an exemplary embodiment, culture vessel 20 is sized to support a plurality of plant embryos (e.g., 10, 100, 1000, 10,000, etc.) through the development process. According to further exemplary embodiments, culture vessel 20 is configured to hold any number of plant tissues through the various stages of development.

Culture vessel 20 is shown as a substantially rectangular (e.g., square, etc.) container including a first portion (e.g., lid, closure, top, etc.), shown as a cover portion 22, coupled to a second portion (e.g., bottom, receptacle, etc.), shown as a base portion 24. Cover portion 22 is coupled to base portion 24 such that culture vessel 20 may be selectively moved between a first or closed position (wherein the contents of culture vessel 20 are substantially concealed) and a second or open position (wherein the contents of culture vessel 20 can be physically accessed). According to an exemplary embodiment, culture vessel 20 has a width of approximately nine inches, a length of approximately nine inches and a height of approximately three fourths of an inch. According to the various exemplary embodiments, culture vessel 20 may be provided in any of a number of sizes.

It should further be noted that culture vessel 20 may be configured in a wide variety of shapes to accommodate varying design criteria, for example, as a generally rectangular shaped vessel as illustrated in the FIGURES. According to the various alternative embodiments, culture vessel may be configured as other well-known or otherwise suitable shapes having linear surface and/or nonlinear edges and surfaces. For example, culture vessel 20 may be a generally circular, octagonal, etc. Further still, culture vessel 20 may be designed for use during only one or more specific steps in the development process.

Referring to FIG. 15 in particular, cover portion 22 has an end wall 26 (e.g., platform, top, top surface, etc.) and a side wall 28 (skirt, peripheral surface, etc.) extending downward therefrom at an orientation that is angled slightly outward from end wall 26. According to an exemplary embodiment, end wall 26 includes a relatively flat outer surface that facilitates the organization of the vessels relative to each other (e.g., by stacking of one culture vessel on top of another, etc.). According to the various alternative embodiments, cover portion 22 may not include a side wall or may included a side wall configured to substantially align with or fit within a corresponding structure on base portion 24.

Referring to FIG. 16, base portion 24 is shown according to an exemplary embodiment. Base portion 24 has an end wall 30 (e.g., platform, bottom, bottom surface, etc.) and a side wall 32 extending upward therefrom at an orientation that is angled slightly outward from end wall 30. Side wall 32 is designed to be at least partially covered (e.g., overlapped, etc.) by side wall 28 of cover portion 22 when culture vessel 20 is in the closed position. Side wall 32 defines an aperture 34 (e.g., cavity, receptacle, etc.) suitable for receiving substances used in the production process including, but not limited to media for plating and tissue cultures. The size and shape of aperture 34 may vary depending on a number of factors, including the size, shape, and quantity of articles to be provided therein. Aperture 34 may be divided into one or more compartments (e.g., sections, storage wells, etc.) for separating one or more plant embryos during the production process.

According to the embodiment illustrated, there is no latching device provided between cover portion 22 and base portion 24 to secure cover portion 22 in the closed position. In such an embodiment, the weight of cover portion 22, in combination with the overlap existing between side wall 28 and side wall 32, help retain cover portion 22 in the closed position. Since culture vessel 20 does not include a latching device, removal of cover portion 22 (either manually or by apparatus 10) may be done quickly and more efficiently. For example, according to the embodiment illustrated, cover portion 22 can be removed by moving at least one of cover portion 22 and base portion 24 relative to the other one of cover portion 22 and base portion 24 in a substantially vertical direction. According to the various alternative embodiments, culture vessel 20 may include any known or otherwise suitable latching device for securing cover portion 22 to base portion 24 in the closed position.

According to an exemplary embodiment, top portion 22 and base portion 24 are formed of a relatively transparent material so that objects within culture vessel 20 can be readily inspected without requiring culture vessel 20 to be moved to the open position. Further, as detailed above, culture vessel 20 is often placed within a growth or development room for an extended period of time after an operation is performed by apparatus 10. Forming cover portion 22 and base portion 24 of a relatively transparent material allows light to pass through culture vessel 20 which may allow culture vessel 20 to remain in the closed position when placed within such a growth or development room. According to an exemplary embodiment, cover portion 22 and base portion 24 are formed of a plastic material such as clear polystyrene. According to the various alternative embodiments, cover portion 22 and base portion 24 may be formed of any known or otherwise suitable transparent material (e.g., glass, etc.). According to still further alternative embodiments, one or more of cover portion 22 and base portion 24 may be formed entirely or partially of a relatively non-transparent material.

According to an exemplary embodiment, culture vessels 20 include an identification device (not shown), such as a barcode, a radio frequency identification (RFID) tag or the like upon which certain information relating to the particular culture vessel 20 may be stored. For example, the identification device may contain information pertaining to what stage in the production process the contents of culture vessel 20 are at so that an culture vessel 20 does not inadvertently repeat and/or miss a step in the production process. Further, the identification device may contain information pertaining to the attributes (e.g., species, etc.) of the plant embryos being developed in culture vessel 20.

One or more receiving devices or readers (not shown) can be provided at apparatus 10 to obtain the information stored upon the identification device corresponding to a particular culture vessel 20. Such a reader can be coupled to controller 90 of apparatus 10 so that information about the delivered culture vessels 20 can be used in determining what operation will be performed on culture vessels 20 at operational station 14 and/or so that information about the delivered culture vessels 20 can be displayed or be otherwise made available to an operator at apparatus 10.

According to an exemplary embodiment, the identification and reader devices may be part of a larger indexing or warehousing system. For example, in industrial applications it may be desirable to track the location and/or progress of various culture vessels 20 at any given time in the production process. Such a warehousing system may be incorporated into an automated transport system that selectively moves culture vessels 20 to and from various locations in the plant including a growth or development room and apparatus 10.

In operation, first rack system 40 of input station 14 is configured to receive a first set of culture vessels 20, referred to as a first batch of culture vessels 20. As detailed above, the delivery of the first batch of culture vessels 20 to input station 14 may be automated or manual. Culture vessels 20 may be empty when they arrive at input station 14 (e.g., if undergoing an initial base media plating operation, etc.) or may be supporting contents therein (e.g., if undergoing a subsequent inspection operation, etc.). Once arranged within first rack system 40, culture vessels 20 are moved one-by-one by transport system 18 to operational station 14 to undergo a first operation (e.g., a plating operation, etc.). After the first operation is completed at operational station 14, the culture vessel 20 is moved to output station 16 by transport system 18 and arranged in second rack system 82. After all of the culture vessels 20 have undergone the first operation, and are arranged at second rack system 82, the batch of culture vessels 20 is moved away from apparatus 10 and taken to a growth or development room. Alternatively, the batch of culture vessels 20 can be moved from second rack system 82 to an auxiliary operation system (e.g., a mass harvesting module, a washing module, etc.) that is coupled to apparatus 10.

After a period of time (e.g., a week, six weeks, etc.), the same batch of culture vessels 20 are brought back to apparatus 10 and arranged within first rack system 40. Once arranged within first rack system 40, culture vessels 20 are moved one-by-one by transport system 18 to operational station 14 to undergo a second operation (e.g., an inspection operation, etc.). After the second operation is completed at operational station 14, the culture vessel 20 is moved to output station 16 by transport system 18 and arranged in second rack system 82. After all of the culture vessels 20 have undergone the second operation, and are arranged at second rack system 82, the batch of culture vessels 20 is moved away from apparatus 10 and once again taken to a growth or development room. This process can be repeated until all of the steps of the production process have been completed.

Next, the method of preparing plant tissue for plant production will be discussed using plant embryos as an example. For purposes of this disclosure, the method has been divided into seven steps. According to the various alternative embodiments, the number of steps may be greater or less than seven. For example, additional preliminary steps may be added relating to the development of the embryogenic tissue. Further, certain steps may be eliminated or done in combination with other steps. In step 1, a batch of empty culture vessels 20 are loaded into apparatus 10 at input station 12. The culture vessels 20 are moved to operational station 14 at which time manipulation system 52 removes cover portion 22 of culture vessel 20 from base portion 24. With cover portion 22 removed, dispensing system 50 applies a base media to culture vessel 20 via nozzle 72. Cover portion 22 is then returned to base portion 24 and culture vessel is moved to output station 16. Referring to FIGS. 12A-12E, the dispensing operation is shown sequentially according to an exemplary embodiment. This is repeated for all of the culture vessels 20 within this batch.

In step 2, the same batch of culture vessels 20 are again loaded into apparatus 10 at input station 12. The culture vessels 20 are moved to operational station 14 at which time manipulation system 52 (using vacuum heads 56) removes cover portion 22 of culture vessel 20 from base portion 24. With cover portion 22 removed, dispensing system 50 applies a embryogenic tissue to the base media already within culture vessel 20 via nozzle 72. When applying the embryogenic tissue, robotic arm 76 may move nozzles 72 at a speed between approximately 10 millimeters per second (mm/sec) and approximately 800 mm/sec. For example, robotic arm 76 may move nozzles 72 laterally across the width of culture vessel 20 at a speed of approximately 75 mm/sec.

According to an exemplary embodiment, the embryogenic tissue is "bulked up" in a bioreactor that is coupled directly to pump 74 which is in turn coupled nozzle 72. According to an exemplary embodiment, between approximately one and ten embryogenic tissue channels or lanes are formed in culture vessel 20. For example, approximately six embryogenic tissue lanes may be formed in culture vessel 20 (e.g., one created by each nozzle 72, etc.). Once the embryogenic tissue is deposited, cover portion 22 is returned to base portion 24 and culture vessel is moved to output station 16. This is repeated for all of the culture vessels 20 within this batch. At this time, the batch of culture vessels 20 is moved to a growth or development room where it will stay for an extended period of time.

In step 3, the same batch of culture vessels 20 are again loaded into apparatus 10 at input station 12. The culture vessels 20 are moved to operational station 14 at which time cameras 55 of imaging system 54 are used to capture images of the plant embryos. This data is sent to controller 90 and is used for inspection and monitoring purposes. The inspection of the plant embryos may be conducted with culture vessel 20 in the closed position since culture vessel 20 is formed of a relatively transparent material. Alternatively, the inspection can be conducted with culture vessel 20 in the open position. Once the inspection is completed, culture vessel 20 is moved to output station 16. This is repeated for all of the culture vessels 20 within this batch. At this time, the batch of culture vessels 20 is moved to a growth or development room where it will stay for another extended period of time.

In step 4, the same batch of culture vessels 20 are again loaded into apparatus 10 at input station 12. The culture vessels 20 are moved to operational station 14 for harvesting. Apparatus 10 may provide for the mass harvesting of the plant embryos or alternatively may provide for plant embryo sorting before harvesting. For mass harvesting, manipulation system 52 removes cover portion 22 from base portion 24. With cover portion 22 removed, transport system 18 delivers only base portion 24 to a mass harvesting module that is coupled to apparatus 10. For sorting before harvesting, with cover portion 22 removed, manipulation system 52 selectively collects only those plant embryo determined by the image processing software to be worthy of harvesting. Such a determination is based upon on or more attributes of the plant embryos (e.g., size, color, texture, etc.). Once the harvesting is completed, the harvested plant embryos are returned to culture vessel 20 and the culture vessels are stacked at output station 16. Once the operation is completed for all culture vessels 20, the batch is moved to a conditioning room.

In step 5, the same batch of culture vessels 20 are again loaded into apparatus 10 at input station 12. The culture vessels 20 are moved to operational station 14 at which time cameras 55 of imaging system 54 are used to capture images of the conditioned plant embryos. This data is sent to controller 90 and is used for inspection and monitoring purposes. The inspection of the conditioned plant embryos may be conducted with culture vessel 20 in the closed position since culture vessel 20 is formed of a relatively transparent material. Alternatively, the inspection can be conducted with culture vessel 20 in the open position. Once the inspection is completed, culture vessel 20 is moved to output station 16. This is repeated for all of the culture vessels 20 within this batch.

In step 6, the plant embryos are ready for germination. Using the data obtained from the imaging system 54, controller 90 and the image processing software are used to determine which of the plant embryos are strong candidates for germination. Culture vessels 20 may be passed through operational station 14 so that manipulating system 52 can be used to collect those plant embryos selected for germination.

In step 7, another inspection operation (similar to those detailed-above with reference to steps 3 and 5) may take place to ensure that the selected plant embryos should be submitted for germination.

The apparatus and method detailed above provide for a relatively rapid, consistent and highly efficient production process for plant embryos that reduces the costs associated therewith since most, if not all, of the steps the production process can be conducted using a single apparatus.

In addition, because the apparatus can be partially or fully automated, human involvement during the production process is minimized. As a result, (1) fewer humans are necessary to conduct the various operations (e.g., plating, etc.) since the apparatus and method are capable of producing thousands of embryos; (2) there is less chance of contamination caused by human contact with the embryos; (3) greater consistency can be achieved in the production process which leads to better quality control; and (4) there is better control of the production process since all operator input variables are handled by the controller.

It should be noted that according to one exemplary embodiment, the embryonic tissue is from a conifer. For example, the conifer may be pine. Further still, the pine may be a Loblolly pine.

According to other exemplary embodiments, the coniferous tree may be selected from the group consisting of Eastern white pine, Western white, Sugar pine, Red pine, Pitch pine, Jack pine, Longleaf pine, Shortleaf pine, Loblolly pine, Slash pine, Virginia pine, Ponderosa pine, Jeffrey pine, Pond pine, and Lodgepole pine, *Radiata* pine and hybrid crosses thereof. In another preferred embodiment, the coniferous tree is selected from the group consisting of, but not limited to, *Abies alba, Abies amabilis, Abies balsamea, Abies bornmuelleriana, Abies concolor, Abies fraseri, Abies grandis, Abies koreana, Abies lasiocarpa, Abies nordmanniana, Abies procera, Araucaria angustifolia, Araucaria araucana, Araucaria bidwillii, Araucaria cunninghamii, Cedrus atlantica, Cedrus deodara, Chamaecyparis lawsoniana, Chamaecyparis pisifera, Cryptomeria japonica, Cuppressocyparis leylandii, Larix decidua, Larix occidentalis, Metasequoia glyptostroboides, Picea abies, Picea engelmannii, Picea glauca, Picea mariana, Picea pungens, Picea rubens, Picea sitchensis, Pinus banksiana, Pinus caribaea, Pinus contorta, Pinus echinata, Pinus edulis, Pinus elliotii, Pinus jeffreyi, Pinus korariensis, Pinus lambertiana, Pinus merkusii, Pinus monticola, Pinus nigra, Pinus palustris, Pinus pinaster, Pinus ponderosa, Pinus rigida, Pinus radiata, Pinus resinosa, Pinus serotina, Pinus strobus, Pinus sylvestris, Pinus taeda, Pinus virginiana, Pseudotsuga menziesii, Sequoia sempervirens, Sequoiadendron giganteum, Taxodium ascends, Taxodium distichum, Taxus baccata, Taxus brevifolia, Taxus cuspidata, Thuja occidentalis, Thuja plicata, Tsuga canadensis, Tsuga heterophylla*, and hybrid crosses thereof.

Specific examples of each of such coniferous tree includes: *Abies alba*, European silver fir; *Abies amabilis*, Pacific silver fir; *Abies balsamea*, Balsam fir; *Abies bornmuelleriana*, Turkish fir; *Abies concolor*, White fir; *Abies fraseri*, Fraser fir;

*Abies grandis*, Grand fir; *Abies koreana*, Korean fir; *Abies lasiocarpa*, Alpine fir; *Abies nordmanniana*, Nordman fir; *Abies procera*, Noble fir; *Araucaria angustifolia*, Parana pine; *Araucaria araucana*, Monkeypuzzle tree; *Araucaria bidwillii*, Bunya pine; *Araucaria cunninghamii*, Hoop pine; *Cedrus atlantica*, Atlas cedar; *Cedrus deodara*, Deodar cedar; *Chamaecyparis lawsoniana*, Port-Orford-cedar; *Chamaecyparis pisifera*, Sawara cypress; *Cryptomeria japonica*, Japanese cedar (Japanese cryptomeria); *Cuppressocyparis leylandii*, Leyland Cypress; *Larix decidua*, European larch; *Larix occidentalis*, Western larch; *Metasequoia glyptostroboides*, Dawn redwood; *Picea abies*, Norway spruce; *Picea engelmannii*, Englemann spruce; *Picea glauca*, White spruce; *Picea mariana*, Black spruce; *Picea pungens*, Colorado blue spruce; *Picea rubens*, Red spruce; *Picea sitchensis*, Sitka spruce; *Pinus banksiana*, Jack pine; *Pinus caribaea*, Caribbean pine; *Pinus contorta*, lodgepole pine; *Pinus echinata*, Shortleaf pine; *Pinus edulis*, Pinyon pine; *Pinus elliotii*, Slash pine; *Pinus jeffreyi*, Jeffrey Pine; *Pinus korariensis*, Korean pine; *Pinus lambertiana*, Sugar pine; *Pinus merkusii*, Sumatran pine; *Pinus monticola*, Western white pine; *Pinus nigra*, Austrian pine; *Pinus palustris*, Longleaf pine; *Pinus pinaster*, Maritime pine; *Pinus ponderosa*, Ponderosa pine; *Pinus rigida*, Pitch pine; *Pinus radiata*, Radiata pine; *Pinus resinosa*, Red pine; *Pinus serotina*, Pond pine; *Pinus strobus*, Eastern white pine; *Pinus sylvestris*, Scots (Scotch) pine; *Pinus taeda*, Loblolly pine; *Pinus virginiana*, Virginia pine; *Pseudotsuga menziesii*, Douglas-fir; *Sequoia sempervirens*, Redwood; *Sequoiadendron giganteum*, Sierra redwood; *Taxodium ascends*, Pond cypress; *Taxodium distichum*, Bald cypress; *Taxus baccata*, European yew; *Taxus brevifolia*, Pacific or Western yew; *Taxus cuspidata*, Japanese yew; *Thuja occidentalis*, Northern white-cedar; *Thuja plicata*, Western red cedar; *Tsuga canadensis*, Eastern hemlock; *Tsuga heterophylla*, Western hemlock.

According to another exemplary embodiment, the coniferous plant tissue may be a Southern Yellow pine. According to yet another exemplary embodiment, the Southern Yellow pine may be selected from the group consisting of *Pinus taeda, Pinus serotina, Pinus palustris*, and *Pinus elliottii*.

It should further be noted that the apparatus and method detailed above are not limited, however, to the production of only coniferous tree tissues and somatic embryos. According to another exemplary embodiment, the plant tissue, such as embryogenic tissue or a somatic embryo may be from a tree selected from the group consisting of chestnut, ash, beech, basswood, birch, black cherry, black walnut/butternut, chinkapin, cottonwood, elm, eucalyptus, hackberry, hickory, holly, locust, magnolia, maple, oak, poplar, red alder, royal paulownia, sassafras, sweetgum, sycamore, tupelo, willow, and yellow-poplar, and intra- and inter-species hybrid crosses thereof.

It should further be noted that the plant tissue production apparatus and the methods detailed above are not limited to the development of somatic plant embryos, but rather may be applicable to any of variety of plant tissue development processes. For example, the plant tissue production apparatus and the methods detailed above may be used with embryogenic tissues, organogenic tissue, vegetative tissue and/or seeds. Specific examples of tissue cultures include, but are not limited to, apical meristems, callus, petioles, leaf pieces, PLBs (i.e., protocorm-like bodies), protoplasts, root tips, etc. Any such tissue, such as a tissue suspended in a liquid medium, may be distributed across the culture vessel for further growth, inspection and/or data collection. One specific example, would be to distribute vegetative propagules of Eucalyptus ready for differentiation into plantlets across the tissue culture medium surface. After a prescribed time on differentiation medium, successful plantlets may be identifiable via the camera system, counted and then either transferred onto another vessel to finish growth in-vitro or be harvested for ex-vitro grow-out in a greenhouse. Another specific example, would be to use the plant tissue production apparatus and methods detailed above to distribute a relatively small or relatively difficult to germinate seed. For example, mutation screening in *Arabidopsis* could be preformed at a much larger scale enabling multiple seedlings (e.g., tens of thousands, etc.) to be screened efficiently.

It is also important to note that the construction and arrangement of the elements of plant tissue production apparatus 10 as shown in the exemplary embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the plant tissue production apparatus may be constructed from any of a wide variety of materials that provide sufficient strength or durability, in any of a wide variety of colors, textures and combinations. Accordingly, all such modifications are intended to be included within the scope of the present inventions. Other substitutions, modifications, changes and omissions may be made in the design, operating conditions and arrangement of the preferred and other exemplary embodiments without departing from the spirit of the appended claims.

The order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes and omissions may be made in the design, operating configuration and arrangement of the preferred and other exemplary embodiments without departing from the spirit of the appended claims.

What is claimed is:

1. A method of preparing plant tissue for plant production with an automated system comprising:
   (a) transporting one or more culture vessels from a first station that includes a first rack system configured to support one or more culture vessels to a second station comprising an automated member configured to manipulate one or more culture vessels and further comprising a dispensing system configured to dispense a substance to one or more culture vessels when in open position;
   (b) manipulating the culture vessels with an automated member, wherein the automated member is configured to manipulate one or more culture vessels by selectively moving one or more culture vessels between a closed position and an open position; and wherein the automated member comprises a robotic arm that has at least one degree of freedom and comprises vacuum heads coupled to a vacuum system, the vacuum heads configured to engage one or more culture vessels;
   (c) dispensing at least one substance to the culture vessels at the second station, wherein the substance is base media or one or more of a somatic embryo, embryogenic tissue, organogenic tissue, vegetative tissue and seed in the form of a liquid suspension culture, and wherein the dispensing system is in fluid communication with at least one reservoir containing the suspension culture;

(d) moving one or more culture vessels to a third station comprising a second rack system configured to support one or more culture vessels;

(e) controlling with a controller steps (a)-(d) and (f) optionally repeating and of steps (a)-(e) one or more times.

2. The method of claim 1, wherein the substance includes a base media.

3. The method of claim 2, further comprising the step of reconfiguring the second station and supplying a different substance to the one or more culture vessels, wherein the different substance includes one or more of a somatic embryo, embryogenic tissue, organogenic tissue, vegetative tissue and seed.

4. The method of claim 1, further comprising the steps of inspecting and monitoring the development of plant tissue in one or more culture vessels at the second station.

5. The method of claim 4, wherein the steps of inspecting and monitoring the development of plant tissue in one or more culture vessels comprise using an imaging system comprising one or more cameras coupled to the controller.

6. A method of preparing plant tissue for plant production with an automated system comprising:

transporting one or more culture vessels from a first station that includes a first rack system configured to support one or more culture vessels to a second station comprising an automated member configured to manipulate one or more culture vessels and further comprising a dispensing system configured to dispense a substance to one or more culture vessels when in open position;

manipulating the culture vessels with an automated member, wherein the automated member is configured to manipulate one or more culture vessels by selectively moving one or more culture vessels between a closed position and an open position; and wherein the automated member comprises a robotic arm that has at least one degree of freedom and comprises vacuum heads coupled to a vacuum system, the vacuum heads configured to engage one or more culture vessels;

performing a first operational step on one or more culture vessels at the second station;

controlling with a controller the steps of transporting and manipulating the culture vessels and performing the first operational step; and reconfiguring at least one of the second station and the controller so that a second operational step can be performed on one or more culture vessels at the second station, the second operational step being different than the first operational step.

7. The method of claim 6, wherein the first operational step is at least one of media plating and tissue plating, and the second operational step is at least one of plant tissue inspection, quality assessment and plant tissue sorting.

8. The method of claim 1, wherein the dispensing system comprises nozzles, and wherein the robotic arm moves the nozzles at a speed between 10 mm/sec and 800 mm/sec.

9. The method of claim 1, further comprising using data obtained from the imaging system to select and collect plant embryos for germination.

10. The method of claim 7, further comprising the steps of inspecting and monitoring the development of plant tissue in one or more culture vessels at the second station.

11. The method of claim 10, wherein the steps of inspecting and monitoring the development of plant tissue in one or more culture vessels comprise using an imaging system comprising one or more cameras coupled to the controller.

12. The method of claim 11, further comprising using data obtained from the imaging system to select and collect plant embryos for germination.

* * * * *